(12) United States Patent
Marsh et al.

(10) Patent No.: US 10,968,490 B2
(45) Date of Patent: Apr. 6, 2021

(54) LABELLING COMPOUNDS AND THEIR USE IN ASSAYS

(71) Applicant: Atlas Genetics Limited, Trowbridge (GB)

(72) Inventors: Barrie J. Marsh, Trowbridge (GB); Christopher G. Frost, Trowbridge (GB); Jonathan Sharp, Trowbridge (GB)

(73) Assignee: Binx Health Limited, Trowbridge (GB)

( * ) Notice: Subject to any disclaimer, the term of this patent is extended or adjusted under 35 U.S.C. 154(b) by 0 days.

(21) Appl. No.: 15/783,130

(22) Filed: Oct. 13, 2017

(65) Prior Publication Data

US 2018/0037937 A1 Feb. 8, 2018

Related U.S. Application Data

(63) Continuation of application No. 15/026,454, filed as application No. PCT/GB2014/053031 on Oct. 8, 2014, now Pat. No. 9,822,398.

(30) Foreign Application Priority Data

Oct. 8, 2013 (GB) ..................... 1317787
Aug. 6, 2014 (GB) ..................... 1413931

(51) Int. Cl.
| | |
|---|---|
| C12Q 1/689 | (2018.01) |
| C07F 17/02 | (2006.01) |
| C12Q 1/6816 | (2018.01) |
| C07F 15/02 | (2006.01) |
| G01N 27/327 | (2006.01) |
| G01N 33/58 | (2006.01) |

(52) U.S. Cl.
CPC .............. *C12Q 1/689* (2013.01); *C07F 15/02* (2013.01); *C07F 17/02* (2013.01); *C12Q 1/6816* (2013.01); *G01N 27/3276* (2013.01); *G01N 33/58* (2013.01); *C12Q 2563/113* (2013.01)

(58) Field of Classification Search
CPC . C12Q 1/689; C12Q 1/6816; C12Q 2563/113
See application file for complete search history.

(56) References Cited

U.S. PATENT DOCUMENTS

| | | |
|---|---|---|
| 5,082,539 A | 1/1992 | Saji et al. |
| 2002/0121314 A1 | 9/2002 | Tao et al. |
| 2003/0143556 A1 * | 7/2003 | Blackburn .............. B82Y 15/00 506/4 |

FOREIGN PATENT DOCUMENTS

| | | |
|---|---|---|
| CN | 103601761 A | 2/2014 |
| JP | H02-83386 A | 3/1990 |
| WO | WO-03/074731 A2 | 9/2003 |
| WO | WO-2005/005657 A1 | 1/2005 |
| WO | WO-2009/061941 A2 | 5/2009 |
| WO | WO-2011/073675 A2 | 6/2011 |
| WO | WO-2012/085591 A1 | 6/2012 |
| WO | WO-2013/190328 A1 | 12/2013 |

OTHER PUBLICATIONS

Allali et al., "Al(OTf)3 as a new efficient catalyst for the direct nucleophilic substitution of ferrocenyl alcohol substrates. Convenient preparation of ferrocenyl-PEG compounds," Tetrahedron Letters. 2012; 53(21): 2604-2607.
Hayashi et al., "Asymmetric synthesis catalyzed by chiral ferrocenylphosphine-transition metal complexes. 5. Palladium-catalyzed asymmetric allylation of active methine compounds," J. Org. Chem. 1988; 53:113-120.
Shipovskov et al., "Electrochemical sandwich assay for attomole analysis of DNA and RNA from beer spoilage bacteria *Lactobacillus brevis*," Biosensors and Bioelectronics. 2012; 37:99-106.
Yu et al., "Preparation of polymer-supported phosphine from ferrocene for palladium-catalyzed Suzuki-Miyaura cross-coupling reactions," Chinese Chemical Letters. 2007; 18: 37-40.
International Preliminary Report on Patentability for Application No. PCT/GB2014/053031 dated Dec. 23, 2015.
Hillier et al., An electrochemical study of enzymatic oligonucleotide digestion. Bioelectrochemistry. Jun. 2004;63(1-2):307-10.
Metay et al., Synthesis and conformational analysis of redox-active ferrocenyl-calixarenes. Tetrahedron. 2009;65(3):672-6.
Pearce et al., Evaluation of a novel electrochemical detection method for Chlamydia trachomatis: application for point-of-care diagnostics. IEEE Trans Biomed Eng. Mar. 2011;58(3):755-8.
Riant et al., An Efficient Asymmetric Synthesis of 2-Substituted Ferrocenecarboxaldehydes. J Org Chem. 1997;62(20):6733-45.
Ihara, et al., "DNA conjugates bearing a ferrocenyl group in backbone and their electrochemical behaviour," Supramolecular Chemistry, vol. 21, Nos. 3-4, Apr.-Jun. 2009, pp. 207-217.
Siemeling, et al., "Aspects of the chemistry of the mixed ferrocene [MeO(CH2CH2O)3(CH2) 3C5Me4]Fe(C5H5). Generation of the unusual α-ferrocenyl carbocation {[MeO(CH2CH2O)3(CH2)3C5Me4]Fe(C5H4 CH2)}," Journal of Organometallic Chemistry, 475 (1994), pp. 229-232.

* cited by examiner

*Primary Examiner* — Pancham Bakshi

(74) *Attorney, Agent, or Firm* — Brown Rudnick LLP; Thomas C. Meyers

(57) ABSTRACT

The invention provides monoferrocenyl compounds of general formula I. The invention also provides substrates labelled with the compounds, functionalised derivatives of the compounds and methods of using the compounds, functionalised derivatives and labelled substrates in electrochemical assays.

5 Claims, 2 Drawing Sheets

LABELLING COMPOUNDS AND THEIR USE IN ASSAYS

CROSS-REFERENCES TO RELATED APPLICATIONS

This application is a continuation of U.S. patent application Ser. No. 15/026,454 entitled "Labelling Compounds and Their Use in Assays," filed on Mar. 31, 2016, which is a national stage application, filed under 35 U.S.C. § 371, of International Application No. PCT/GB2014/053031, filed on Oct. 8, 2014, and claims the benefit of, and priority to, GB Patent Application No. 1413931.5 filed on Aug. 6, 2014, and GB Patent Application No. 1317787.8 filed on Oct. 8, 2013, the complete contents of which are hereby incorporated herein by reference in their entirety for all purposes.

FIELD OF THE INVENTION

The invention relates to ferrocenyl labelling compounds and the use of such compounds in electrochemical assays and electrochemical detection methods.

BACKGROUND OF THE INVENTION

The detection of certain biological molecules plays an important part in many aspects of life. For example, in the medical field, there is an ever-present need to detect bacterial or viral pathogens, or biological molecules. Other fields in which sensitive assays are essential include the food and beverage industries. One method of detection involves the use of electrochemically active compounds. The application of electrochemical detection has a number of advantages over other methods, such as fluorescent detection. Electrochemical detection has the potential for very high levels of sensitivity and exhibits a wider linear dynamic range than fluorescence. Furthermore, there is no requirement for samples to be optically clear. There is also less interference from background contaminants (many biological samples auto-fluoresce).

WO03/074731 discloses electrochemically active markers and methods of probing for a nucleic acid. The methods involve contacting a nucleic acid solution with an oligonucleotide probe attached to an electrochemically active marker. The probe is caused to at least partially hybridise with any complementary target sequence which may be present in the nucleic acid solution. Following enzymatic degradation of the nucleic acid probe, information is electrochemically determined relating to the marker.

Hillier et al (Bioelectrochemistry 63 (2004) 307-310) describes the use of ferrocene urea compounds as labels in pulse electrochemical methods for the electrochemical discrimination between a labelled oligonucleotide and an enzyme digested labelled oligonucleotide.

WO2005/005657 discloses further electrochemically active markers and methods of detecting protease activity. The methods involve contacting a sample solution with a protease substrate attached to an electrochemically active marker, providing conditions under which any protease present in the sample can degrade the protease substrate. Following degradation, information is electrochemically determined relating to the marker.

WO2012/085591 and WO2013/190328 describe certain diferrocenyl compounds for use as electrochemical labels.

There is a continuing need to develop labels that enable detection of the presence of biological substrates or indicators, for example, nucleic acids or amino acids, in low concentrations. In particular, there is a continuing need for new labels with different oxidation potentials and/or with different chemical or physical properties thereby widening the range of possible assays available and increasing the scope for the development of multiplex reactions. Furthermore there is a need for electrochemically active compounds which can be used as internal controls in assays. Such compounds need to give robust, consistent electrochemical responses.

SUMMARY OF THE INVENTION

The present invention provides new ferrocenyl labelling compounds, functionalised derivatives of the compounds and substrates labelled with the compounds. The compounds of this invention have been found to be effective labels for use in electrochemical assays. The compounds of the invention have also been found to give robust, consistent electrochemical responses with oxidation potentials between −150 mV and 584 mV, so they may be useful as internal controls in assays. When used as probes in assays, the compounds of the invention give consistent and reproducible peak heights.

Furthermore, the compounds of the invention exhibit a large electrochemical range, allowing excellent tuning for an internal control label to be in a "clean" area of the voltammogram i.e. in an area removed from other peaks. Thus, the compounds of the invention are very useful in multiplex assays.

The compounds and labelled substrates of the invention may be used in any other electrochemical technique in which their electrochemical characteristics can be utilised to derive information about the labels or their environment.

An embodiment of the invention provides a compound having general formula I

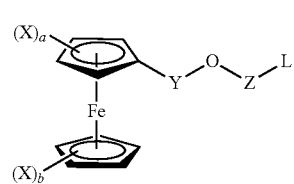

wherein:
  each X substituent is independently selected from halo, vinyl, alkyl, cycloalkyl, $SiR_3$, $SnR_3$, $PR_2$, $P(O)R_2$, SR, S(O)R, $SO_2R$, aryl, heteroaryl, CHO, $CO_2R$, CN and $CF_3$;
  each R is independently selected from alkyl, cycloalkyl, aryl and heteroaryl;
  Y is a spacer;
  Z is a spacer;
  L is a linker group;
  a is 0, 1, 2, 3 or 4;
  b is 0, 1, 2, 3, 4 or 5; and
  vinyl, alkyl, cycloalkyl, alkylene, aryl and heteroaryl may optionally be substituted with 1, 2 or 3 substituents independently selected from unsubstituted alkyl, OH, CN, fluorine, chlorine, bromine and iodine.

The labelling compounds of the invention and the labelled substrates derived therefrom offer characteristics which make them useful complements to previously known labelling compounds, permitting a wider spectrum of applications. For example, the compounds and labelled substrates of the invention may offer additional opportunities for avoidance of conditions under which measurement potential may be compromised by interference with impurities that may be present. The compounds and labelled substrates of the invention also offer differing electrochemical potential values, potentially allowing greater flexibility in multiplex assays.

Electrochemical activity of a marker is primarily modulated by the substituents on the ferrocenyl group. Therefore choice of X, a and b can allow the electrochemical potential of the compound to be selected appropriately. Further fine tuning can be achieved by the choice of Y and Z.

In an embodiment, the invention relates to a compound of general formula IA

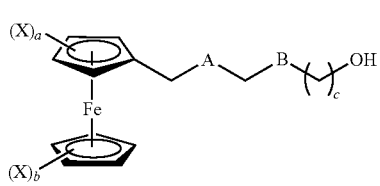

wherein:
each X substituent is independently selected from halo, vinyl, alkyl, cycloalkyl, $SiR_3$, $SnR_3$, $PR_2$, $P(O)R_2$, SR, S(O)R, $SO_2R$, aryl, heteroaryl, CHO, $CO_2R$, CN and $CF_3$;
each R is independently selected from alkyl, cycloalkyl, aryl and heteroaryl;
A is O, B is $CH_2$ and c is 1, or
A is $CH_2$, B is O and c is 2;
a is 0, 1, 2, 3 or 4;
b is 0, 1, 2, 3, 4 or 5; and
vinyl, alkyl, cycloalkyl, alkylene, aryl and heteroaryl may optionally be substituted with 1, 2 or 3 substituents independently selected from unsubstituted alkyl, OH, CN, fluorine, chlorine, bromine and iodine.

In another embodiment, the invention provides a compound of general formula IB

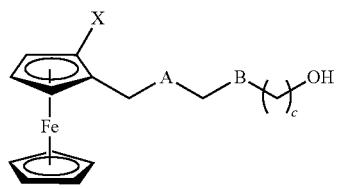

wherein:
each X substituent is independently selected from halo, vinyl, alkyl, cycloalkyl, $SiR_3$, $SnR_3$, $PR_2$, $P(O)R_2$, SR, S(O)R, $SO_2R$, aryl, heteroaryl, CHO, $CO_2R$, CN and $CF_3$;
each R is independently selected from alkyl, cycloalkyl, aryl and heteroaryl;
A is O, B is $CH_2$ and c is 1, or
A is $CH_2$, B is O and c is 2; and
vinyl, alkyl, cycloalkyl, alkylene, aryl and heteroaryl may optionally be substituted with 1, 2 or 3 substituents independently selected from unsubstituted alkyl, OH, CN, fluorine, chlorine, bromine and iodine.

Preferably in the compounds of formula I, Y and Z are both alkylene, either or both of which is/are optionally be substituted with 1, 2 or 3 substituents independently selected from unsubstituted alkyl, OH, CN, fluorine, chlorine, bromine and iodine. More preferably Y is straight-chained alkylene which may be substituted with 1, 2 or 3 substituents independently selected from OH, CN, fluorine, chlorine, bromine and iodine and Z is Cl or C3-C8 alkylene which may be substituted with 1, 2 or 3 substituents independently selected from unsubstituted alkyl, OH, CN, fluorine, chlorine, bromine and iodine.

In the compounds of the invention, L is any linker group suitable for effecting linkage to the substrate either directly or via a functionalising group as described herein. L is advantageously a linker group comprising an oxygen atom. L is preferably a hydroxy group or a protected hydroxy group. Most preferably L is a hydroxy group.

In the compounds of the invention, ferrocenyl may have only one X substituent, such that a+b=1. Ferrocenyl may have no substituent on the distal cyclopentadienyl ring, such that b is 0. Ferrocenyl may have only one substituent on the proximal cyclopentadienyl ring, such that a is 1.

In an embodiment of the compounds of the invention, each X may be independently selected from halo, vinyl, alkyl, cycloalkyl, $SiR_3$, $SnR_3$, $P(O)R_2$, SR, S(O)R, $SO_2R$, aryl, heteroaryl, CHO, $CO_2R$, CN and $CF_3$. In another embodiment of the compounds of the invention, each X may be independently selected from halo, vinyl, SR, S(O)R, alkyl, $P(O)R_2$, $S(O)_2R$, $SiR_3$. In a particular embodiment, each X is independently selected from SR, S(O)R and $S(O)_2R$. In another embodiment, a is 4, b is 5 and each X is methyl.

The compounds of the invention are labelling compounds suitable to form labelled substrates. Attachment of the compounds to a substrate may be direct (e.g. via L) or via a functionalising group, preferably via a phosphoramidite group. Thus, in an embodiment, the invention provides compounds which are functionalised derivatives of the compounds of the invention. Preferably, the functionalised derivatives comprise a functionalising moiety selected from succinimidyl ester groups, phosphoramidite groups, maleimide groups, biotin and azide groups. In a particular embodiment, the functionalising moiety is a phosphoramidite group.

In another embodiment the invention provides substrates labelled with a compound of the invention. Substrates that may be labelled include nucleic acids, amino acids, polypeptides, carbohydrates and derivatives or synthetic analogues of any of those molecules. Other substrates that might be labelled include latex/paramagnetic particles.

In a preferred embodiment, the substrate is a nucleic acid. Preferably the nucleic acid has a sequence which is complementary to a sequence in a microorganism selected from the group consisting of *Chlamydia trachomatis, Trichomonas vaginalis, Neisseria gonorrhoeae, Mycoplasma genitalium* and methicillin resistant *Staphylococcus aureus*. In an embodiment the substrate is not adenosine.

In another preferred embodiment, the substrate is an amino acid, polypeptide or carbohydrate; or a nucleic acid comprising at least 2 nucleotides.

An assay kit for determining the presence of an assay target, wherein the assay kit comprises a labelled substrate of the invention, is also provided.

Another embodiment provides the use of a compound of any of the embodiments of the invention as a label in an electrochemical assay. In a particular embodiment, the assay is for detecting an electrochemically labelled substrate.

More particularly, the assay is for determining the amount of an electrochemically labelled substrate. For example, the compounds of the invention may find use in a method as described in WO03/074731 or in a method as described in WO2005/005657.

Another embodiment provides a method for the manufacture of a functionalised derivative of a compound of formula I, comprising reacting a compound of formula I with a functionalising compound. In a particular embodiment the functionalising compound comprises a phosphoramidite group.

Also provided is a method for the manufacture of a labelled substrate comprising reacting a compound of any of the embodiments of the invention with a substrate to obtain a labelled substrate.

Another embodiment provides a method of detecting a nucleic acid in a sample comprising contacting a nucleic acid with a complementary nucleic acid probe under conditions to allow hybridization between the probe and the nucleic acid, wherein the probe is labelled with a compound of any the embodiments of the invention. The method can include the further step of measuring the electrochemical activity of the compound labelling the probe. Optionally the method comprises the step of selectively degrading the either hybridised or unhybridised probe, prior to the measuring step. Selective degradation of a hybridised probe may be effected by a double strand specific exonuclease enzyme. The electrochemical activity of the compound of the invention may be dependent either quantitatively or qualitatively on the extent of degradation of the probe. Optionally the nucleic acid is amplified (for example by PCR or another nucleic acid amplification technique) prior to contacting it with the probe.

Another embodiment provides a method of detecting a substrate labelled with a compound of any of the embodiments of the invention, comprising the step of measuring the electrochemical activity of the compound. In an embodiment, there is used an assay device comprising at least two labels, each label comprising a compound or labelled substrate according to the invention.

DETAILED DESCRIPTION

Figure 1:
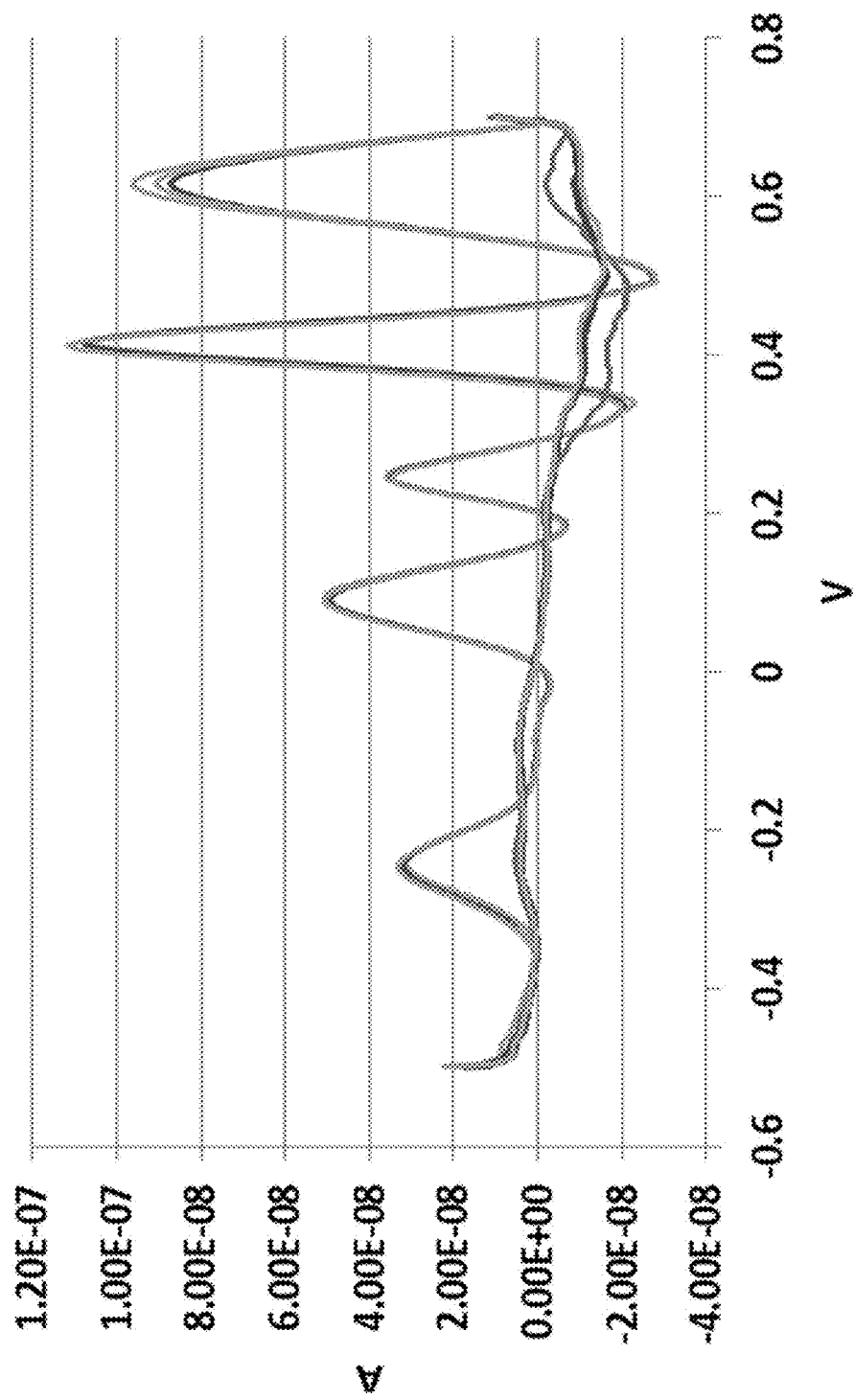
FIG. 1 shows voltammograms obtained from the multiplex PCR assay described in example 22 below.

The term "alkyl" refers to straight-chain alkyl groups having from 1 to 8 carbon atoms, preferably from 1 to 6 carbon atoms, and more preferably from 1 to 4 carbon atoms and branched chain alkyl groups having from 3 to 8 carbon atoms, preferably from 3 to 6 carbon atoms. Illustrative alkyl groups include methyl, ethyl, n-propyl, i-propyl, n-butyl and t-butyl.

The term "cycloalkyl" refers to saturated or partially saturated carbocylic ring having from 3 to 8 ring members, preferably from 3 to 6 ring members. One or more ring members may be selected from heteroatoms such as oxygen, sulphur and nitrogen. Illustrative cycloalkyl groups include cyclohexyl, cyclopentyl, piperidinyl and morpholinyl.

The term "alkylene" refers to a bivalent straight-chained alkyl radical having from 1 to 8 carbon atoms, preferably from 1 to 6 carbon atoms, more preferably having 1 to 4 carbon atoms or a bivalent branched-chain alkyl radical having 2 to 6 carbon atoms, preferably 3 to 4 carbon atoms.

The term "alkenyl" refers to straight- or branched-chain alkenyl groups having from 2 to 6 carbon atoms, more preferably from 2 to 4 carbon atoms. Illustrative alkenyl groups include ethenyl, propenyl and butenyl.

The term "aryl" refers to an unsaturated, aromatic monocyclic or bicyclic ring having from 5 to 10 carbon members. Illustrative aryl groups include phenyl and napthalenyl.

The term "heteroaryl" refers to an aromatic monocyclic or bicyclic aromatic ring system having 5 to 10 ring members and which contains carbon atoms and from 1 to 4 heteroatoms independently selected from heteroatoms such as oxygen, sulphur and nitrogen. Illustrative heteroaryl groups include furanyl, imidazolyl and thiazolyl.

"Halo" or "halogen" refers to fluorine, chlorine, bromine and iodine.

The term "proximal cyclopentadienyl ring" refers to the cyclopentadienyl ring to which the spacer group Y is attached. The term "distal cyclopentadienyl ring" refers to the cyclopentadienyl ring to which the spacer group Y is not attached.

With reference to substituents, the term "independently" refers to the situation where when more than one substituent is possible, the substituents may the same or different from each other.

Except where the contrary is apparent from the context, references to the term "substrate" are to be understood to include both naturally occurring substrates and synthetic substrates. References to carbohydrates, nucleic acids, amino acids and polypeptides, are to be understood as referring to naturally occurring or synthetic carbohydrates, nucleic acids, amino acids and polypeptides.

The term "polypeptide" refers to any chain of amino acids linked by peptide bonds comprising two or more amino acid residues, such as a dipeptide or a complex protein.

The term "nucleic acid" refers to a molecule comprising one or more nucleic acid residues and includes nucleotides, nucleosides, oligonucleotides and polynucleotides, and includes DNA and RNA. The nucleic acid may comprise 1 to 50 nucleotides, more preferably from 2 to 40 nucleotides especially from 15 to 35 nucleotides, with from 18 to 30 nucleotides being especially preferred. For some applications, shorter length substrates may be useful, for example nucleic acid with from 1 to 14 nucleotides, more preferably from 2 to 10 nucleotides. Nucleotides may be selected from adenosine, thymidine, guanosine, cytidine or uridine nucleotides. When the nucleic acid is attached to a label provided herein, it is preferably attached through a group attached to the ribose or deoxyribose group of a nucleotide, for example in the 2', 3' or 5' position, such as through an oxygen or nitrogen atom. Most preferably, the nucleic acid is attached at the 3' or 5' position of a nucleotide, for example at the 5' position. The sequence of the nucleic acid portion of the substrate is preferably such that the substrate is able to hybridise with a complementary target sequence and thus be used as a probe in a molecular biological technique, for example, one of the nucleic acid detection techniques disclosed herein.

The term "carbohydrate" refers to a molecule comprising one or more saccharide residue and includes monosaccharides, oligosaccharides, and polysaccharides.

Substrates can be single nucleotides and single amino acids. In the case of an assay relying upon cleavage of a substrate, for example by an enzyme, a single amino acid or nucleotide may be regarded as a substrate because, although it lacks an internal bond capable of being cleaved by an enzyme, such a bond may be formed through the attachment of a marker. In an embodiment the substrate is not adenosine.

Where derivatives of naturally occurring substrates are referred to herein, those derivatives may be naturally occurring derivatives or synthetic derivatives of the substrate.

References to the term "hybridise" in the context of nucleic acids will be understood to mean specific binding of a first nucleic acid to a second nucleic acid of complementary sequence. It will also be understood that in order for hybridisation to occur the complementarity of nucleic acid sequences is not required to be total. Hybridisation includes complementary binding that includes base mis-match to the extent that such mis-match shall not materially reduce the efficiency of the methods described.

A compound of the invention as described above may be attached directly to a substrate, or after functionalisation of the compound and/or or after derivatisation of the substrate.

A functionalised derivative according to the invention may be a compound according to formula II:

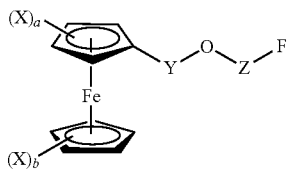

II wherein:
each X substituent is independently selected from halo, vinyl, alkyl, cycloalkyl, $SiR_3$, $SnR_3$, $PR_2$, $P(O)R_2$, SR, S(O)R, $SO_2R$, aryl, heteroaryl, CHO, $CO_2R$, CN and $CF_3$;
each R is independently selected from alkyl, cycloalkyl, aryl and heteroaryl;
Y is a spacer;
Z is a spacer;
F is a functionalising group;
a is 0, 1, 2, 3 or 4;
b is 0, 1, 2, 3, 4 or 5; and
vinyl, alkyl, cycloalkyl, alkylene, aryl and heteroaryl may optionally be substituted with 1, 2 or 3 substituents independently selected from unsubstituted alkyl, OH, CN, fluorine, chlorine, bromine and iodine.

F may be derived from L in the compounds of formula I. Preferably F comprises a succinimidyl ester group, phosphoramidite group, maleimide group, biotin or azide group.

Preferably F is or comprises a phosphoramidite group. The functionalised derivative may therefore be a compound according to formula IIA:

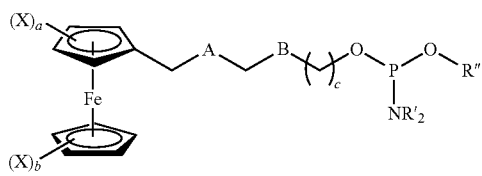

IIA wherein:
each X substituent is independently selected from halo, vinyl, alkyl, cycloalkyl, $SiR_3$, $SnR_3$, $PR_2$, $P(O)R_2$, SR, S(O)R, $SO_2R$, aryl, heteroaryl, CHO, $CO_2R$, CN and $CF_3$;
each R is independently selected from alkyl, cycloalkyl, aryl and heteroaryl;
A is O, B is $CH_2$ and c is 1, or
A is $CH_2$, B is O and c is 2;
R' is alkyl;
R" is alkyl;
a is 0, 1, 2, 3 or 4;
b is 0, 1, 2, 3, 4 or 5; and
vinyl, alkyl, cycloalkyl, alkylene, aryl and heteroaryl may optionally be substituted with 1, 2 or 3 substituents independently selected from unsubstituted alkyl, OH, CN, fluorine, chlorine, bromine and iodine.

Preferably R' is i-propyl and R" is —$CH_2CH_2CN$. Compounds of formula IIA may be formed by functionalisation of a compound of formula IA with a functionalising compound comprising a phosphoramidite group. Functionalisation with phosphoramidite is particularly advantageous for attaching compounds of the invention to nucleic acids. The linking of phosphoramidite groups to nucleic acids is well-known and a routine matter to those skilled in the art.

Labelled substrates according to the invention may be prepared by reaction of a compound or functionalised derivative of the invention, with a substrate. Thus, a labelled substrate may be of formula

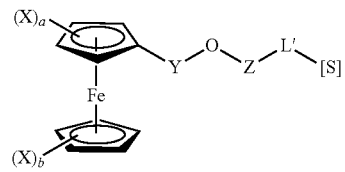

III wherein:
each X substituent is independently selected from halo, vinyl, alkyl, cycloalkyl, $SiR_3$, $SnR_3$, $PR_2$, $P(O)R_2$, SR, S(O)R, $SO_2R$, aryl, heteroaryl, CHO, $CO_2R$, CN and $CF_3$;
each R is independently selected from alkyl, cycloalkyl, aryl and heteroaryl;
Y is a spacer;
Z is a spacer;
L' is the residue of L or F as described above, after a compound or functionalised derivative of the invention is reacted with a substrate;
a is 0, 1, 2, 3 or 4;
b is 0, 1, 2, 3, 4 or 5;
[S] is the residue of a substrate; and
vinyl, alkyl, cycloalkyl, alkylene, aryl and heteroaryl may optionally be substituted with 1, 2 or 3 substituents independently selected from unsubstituted alkyl, OH, CN, fluorine, chlorine, bromine and iodine.

L' may be the residue of L or F as described above, after a compound or functionalised derivative of the invention is reacted with a substrate. Preferably L' is the residue of a hydroxy group or a phosphoramidite group. In an embodiment [S] is not the residue of a single nucleotide. In an embodiment, [S] is the residue of a polypeptide, amino acid or carbohydrate.

Illustrative compounds of the invention are shown in Table 1 below.

TABLE 1

Illustrative compounds of the invention

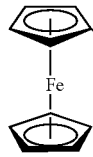
(1)
3-(ferrocenylmethoxy)propan-1-ol

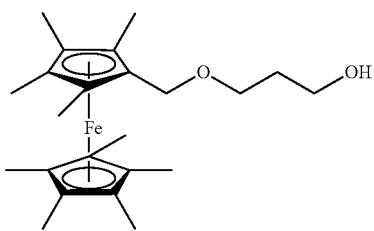
(2)
3-(nonamethylferrocenylmethoxy)propan-1-ol

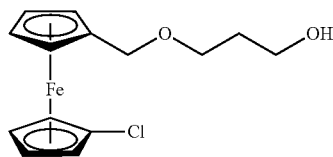
(3)
3-((1'-chloro)-ferrocenylmethoxy)propan-1-ol

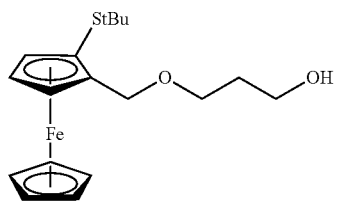
(4)
3-((2-tert-butylthio)-ferrocenylmethoxy)propan-1-ol

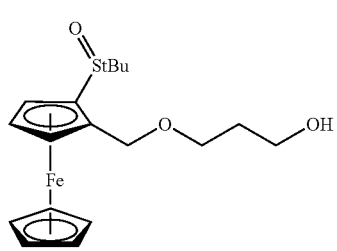
(5)
3-((2-tert-butylsulfinyl)-ferrocenylmethoxy)propan-1-ol

TABLE 1-continued

Illustrative compounds of the invention

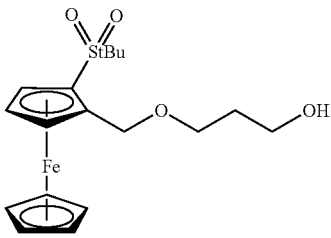
(6)
3-((2-tert-butylsulfonyl)-ferrocenylmethoxy)propan-1-ol

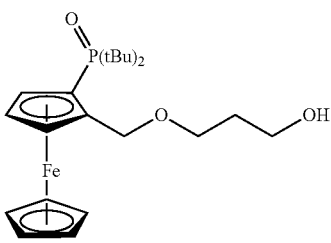
(7)
3-((2-di-tert-butylphospinyl)-ferrocenylmethoxy)propan-1-ol

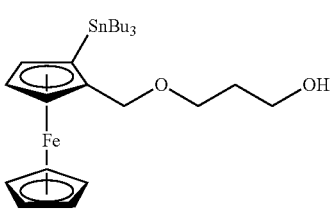
(8)
3-(2-tributylstannyl-ferrocenylmethoxy)propan-1-ol

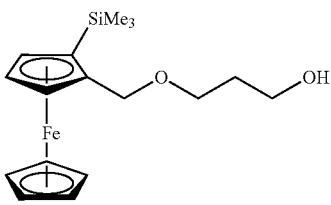
(9)
2-trimethylsilyl-ferrocenylmethoxy)propan-1-ol

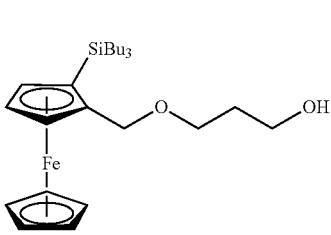
(10)
3-(2-tributylsilyl-ferrocenylmethoxy)propan-1-ol

TABLE 1-continued

Illustrative compounds of the invention

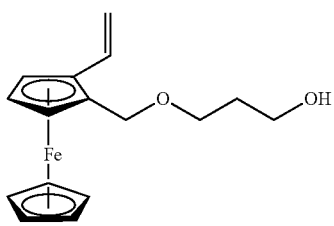

(11) 3-(2-trimethylstannyl-ferrocenylmethoxy)propan-1-ol

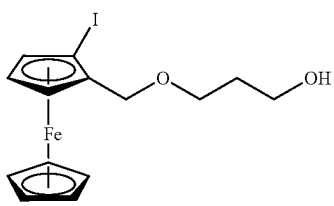

(12) 3-(2-Vinyl-ferrocenylmethoxy)propan-1-ol

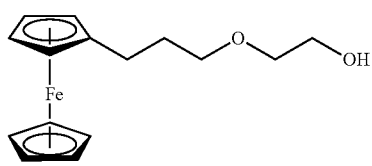

(13) 3-(2-iodo-ferrocenylmethoxy)propan-1-ol

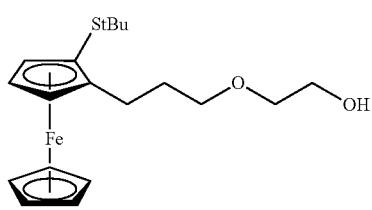

(14) 2-(3-ferrocenylpropoxy)ethanol

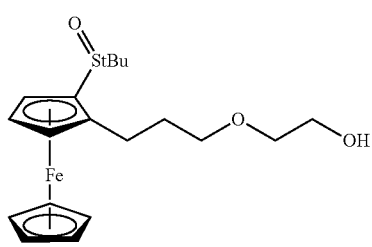

(15) 2-(3-(2-tert-butylthio)-ferrocenylpropoxy)ethanol

(16) 2-(3-(2-tert-butylsulfinyl)-ferrocenylpropoxy)ethanol

TABLE 1-continued

Illustrative compounds of the invention

(17) 2-(3-(2-tert-butylsulfonyl)-ferrocenylpropoxy)ethanol

Any of the compounds in Table 1 may be functionalised by any suitable method, for example by phosphoramidation. Illustrative functionalised compounds of the invention, functionalised with a phosphoramidite group, are shown in Table 2 below. The present invention encompasses labelled substrates derived from the compounds in Table 1 and 2.

TABLE 2

Illustrative functionalised compounds of the invention 2-cyanoethyl-(2(3-ferrocenylpropoxy)ethanol)di-iso-propyl-phosphoramidite 2-Cyanoethyl-(3-(Nonamethylferrocenylmethoxy)propan-1-ol)di-iso-propylphosphoramidite It is believed that compounds of the invention, particularly those having sulfur-containing or phosphorus-containing substituents on the ferrocenyl moiety, and their corresponding functionalised derivatives and labelled substrates, will be useful in assays in which the measurement potential will be relatively high, for example, in excess of 400 mV, for example in excess of 450 mV or even in excess of 500 mV. Compounds having electrochemical potentials of at least 450 mV, for example 500 mV or more, will be particularly useful in extending the range of available potential values and therefore, for example, in potentially providing for more effective multiplex assays. Compounds of the invention having highly electron-withdrawing substituents on the ferrocenyl moiety, for example, trifluoromethyl or cyano, are believed to have similar advantages in terms of offering high electrochemical potential values thereby extending the range of useful labels and labelled substrates. Compounds of the invention that are electron rich, such as compound 2, are useful for extending the range of electrochemical potentials to low voltages, for example to a voltage <0 mV. This is particularly advantageous for extending the scope of multiplex assays.

Additionally, some compounds of the invention, particularly those compounds bearing halogen atoms, and the corresponding labelled substrates offer the advantage of having a narrower voltage peak, which is advantageous in providing for the option of utilising a greater number of labels in a multiplex assay, since the narrower measurement peaks result in wider gaps between peaks, which may be utilised if desired by incorporating additional labels with potentials that will be within the gaps.

Electrochemical detection is based on the observation that an electrochemically active marker exhibits different electrochemical characteristics depending on whether or not it is attached to a substrate and on the nature of the substrate. For example, in the case of an electrochemical label attached to an amino acid, the exhibited characteristics will depend not only on the identity of the amino acid but also on whether or not that amino acid residue is incorporated into a polypeptide, and on the length of any such polypeptide. Under appropriate circumstances, the electrochemical activity of a marker attached to an amino acid residue can change by a detectable degree following loss of attachment of a single or very few amino acid residues.

The size and characteristics of a substrate to which an electrochemically active marker is attached influence the observable characteristics of the electrochemical marker. Without wishing to be bound by theory, such a change in the observable characteristics of the electrochemical may occur, for example, by influencing the rate of migration of the marker by diffusion or its rate of migration in response to an electric field.

Electrochemical activity of a marker may also be influenced by steric effects resulting from the presence of the molecule to which it is linked. For example, steric hindrance may prevent the marker from approaching an electrode and accepting or donating electrons.

If the marker is attached to a polypeptide then the secondary structure of the polypeptide (as largely determined by the primary sequence) may influence the physical properties of the marker. For example, if the marker is attached to an amino acid residue in a polypeptide such that the structure of the polypeptide sterically hinders the electrochemically active marker then the signals observable by voltammetry may be reduced. Digestion of the polypeptide may destroy or release secondary structure elements and thus reduce or abolish the influence of the peptide structure on the marker. Accordingly, digestion of the polypeptide results in a change, usually an increase, in the electrochemical signal produced by the marker moiety. In a differential pulse voltammetry experiment, the Faradaic current response at a particular applied voltage may increase upon digestion of the peptide.

The information relating to the electrochemically active marker can be obtained by voltammetry or by an amperometric method. Differential pulse voltammetry is particularly suitable. If desired, the electrochemical detection step may be carried out using one or more electrodes covered by a membrane which is able to selectively exclude molecules based on one or more characteristics, for example, size, charge or hydrophobicity. That may assist in eliminating background noise current arising from, for example, charged species in the solution.

Analogously, if a marker is attached to a nucleotide, the electrochemical characteristics will be influenced by whether or not the nucleotide is incorporated into a more complex nucleic acid such as a polynucleotide, upon the length of that nucleic acid, and upon the sequence of the nucleic acid, especially in the vicinity of the point of attachment.

The invention also provides a method of detecting a nucleic acid (for example RNA or DNA) in a sample comprising the optional step of amplifying the nucleic acid (for example by PCR or another nucleic acid amplification technique) followed by the step of contacting the amplicon (or the nucleic acid) with a complementary nucleic acid probe under conditions to allow hybridization between the probe and amplicon (or the nucleic acid), followed by the step of selectively degrading either hybridised or unhybridised probe (for example by use of single or double strand specific nucleases), wherein said probe is labelled with an electrochemically active compound of the invention and wherein the method provides the step of measuring the electrochemical activity of the compound labelling the probe of wherein said electrochemical activity is dependent either quantitatively or qualitatively on the extent of degradation of the probe. Such use of electrochemical labels in nucleic acid hybridisation assays is described by Pearce et al. (2011) *IEEE Trans Biomed Eng* 58:755-58, the complete contents of which are incorporated herein by reference.

The invention also provides a method of detecting an antibody or derivative (which may for example be bound to target antigen in an assay) with an electrochemically active compound of the invention comprising the step of measuring the electrochemical activity of the compound. This method can be performed quantitatively or qualitatively.

The invention also provides methods of diagnosing or monitoring a disease in a subject comprising using a method of the invention in the detection of a protease or a protease inhibitor associated with said disease in a tissue or body fluid of the subject. A substrate for the protease can be labelled according to the invention. Examples of disease that are associated with the presence of a protease or a protease inhibitor in a tissue of the subject include hereditary predisposition to thromoembolism caused to deficiencies in anti-thrombin III in the blood serum. Elevated serum or extracellular matrix cathepsin levels may be indicative of Alzheimer's disease, cancer or arthritis. Preferably the tissue or body fluid of the subject is serum, plasma, saliva, urine or any other tissue or body fluid of which a sample may be conveniently and safely obtained.

The invention also provides methods of diagnosing a disease in a subject comprising using a method of the invention to detect a polypeptide associated with said disease in a tissue or body fluid of the subject.

The invention also provides methods of diagnosing or monitoring a disease in a subject comprising using a method of the invention in the detection of a nuclease or a nuclease inhibitor associated with said disease in a tissue or body fluid of the subject.

Furthermore, the invention provides use of a method of the invention for detecting a disease in a subject. The invention also provides methods of detecting a microorganism (in particular, a pathogen or other undesirable organism, for example a food spoilage organism), comprising using a method of the invention. A substrate from the microorganism (or derived from the pathogen e.g. a nucleic acid amplicon produced using a target nucleic acid sequence in the pathogen) can be labelled according to the invention. Detection of the labelled substrate can be used to indicate detection of the microorganism. Preferably the microorganism is selected from the group consisting of *Chlamydia trachomatis, Trichomonas vaginalis, Neisseria gonorrhoeae, Mycoplasma genitalium* and methicillin resistant *Staphylococcus aureus*.

The invention also provides an assay comprising a step which uses a labelled substrate of the invention, optionally in combination with other assay components for example a sample vessel, a container comprising electrodes for electrochemical detection, enzymes for use in the assay or standards and controls. Said assay may use more than one different labelled substrate of the invention. If that is the case the presence of different labelled substrates may be differentially detected by labelling them with electrochemical labels of the invention having different electrochemical characteristics (for example different oxidation potentials) thereby permitting the assay to be a multiplex (for example a duplex) assay in which different substrates may be discriminated when present in the same sample vessel. Simplex assays are also encompassed by the invention.

As illustrated in the examples, incorporation of one or more substituents on the ferrocenyl groups can be used to obtain compounds with modified electrochemical characteristics to be used in assays. Moreover, the invention provides a range of compounds from which two or more may be selected for use in multiplex reactions and assays.

Attachment of a compound or a functionalised derivative of the invention to a substrate can be by any suitable linkage, typically by linkage to a substrate side chain. Conventional hydroxy protecting groups, for example those described by T. W. Greene and P. G. M. Wuts in "Protective groups in organic chemistry" John Wiley and Sons, 4th Edition, 2006, may be used. A common hydroxy protecting group suitable for use herein is a methyl ether; deprotection conditions can comprise refluxing in 48% aqueous HBr for 1-24 hours, or by stirring with borane tribromide in dichloromethane for 1-24 hours. Alternatively a hydroxy group may be protected as a benzyl ether; deprotection conditions can comprise hydrogenation with a palladium catalyst under a hydrogen atmosphere.

Various synthetic methods are known in the art for the derivatisation of substrates. For example, lysine or lysine residues may be derivatised by reaction with a succinimidyl ester. For derivatisation of other amino acids and amino acid residues, other known synthetic methods may be used. For example, a maleimide reagent may be used to derivatise cysteine or cysteine residues. An N-hydroxysuccinimide ester may be used to derivatise the amino terminus or side chain amino group of a polypeptide or an amino acid. Suitable derivatisation methods for nucleic acids are also well-known, for example, using a phosphoramidite moiety.

A compound of the invention may be attached to a substrate by use of any functionalising group that facilitates attachment of a labelling compound to a substrate. Suitable functionalising groups include succinimidyl ester groups, phosphoramidite groups, maleimide groups, biotin and azide groups.

Attachment of a compound of the invention to a polypeptide, for example via cysteine or lysine, may be accomplished in some cases by incubation of the polypeptide and compound of the invention together at room temperature in an appropriate buffer solution. Where the label is advantageously to be linked to cysteine or lysine but the substrate sequence does not contain cysteine or lysine at a suitable position the sequence may, if desired, be mutated to add one or more cysteine or lysine residue either as an additional residue or as a substitution for another residue. An alternative method for attachment to polypeptides includes biotinylation of the labels and use of commercial streptavidinated proteins (or vice versa). By way of example, the substrate may be biotinylated by any standard technique for example by use of a commercially available biotinylation kit. Biotinylated substrate will bind to strepavidin or avidin conjugated compounds such as antibodies, which are commercially and widely available.

In an embodiment, the compound of formula I is not

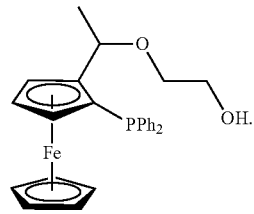

In an embodiment, the compound of formula I is not

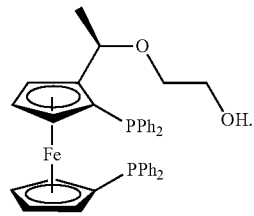

In an embodiment the invention does not include

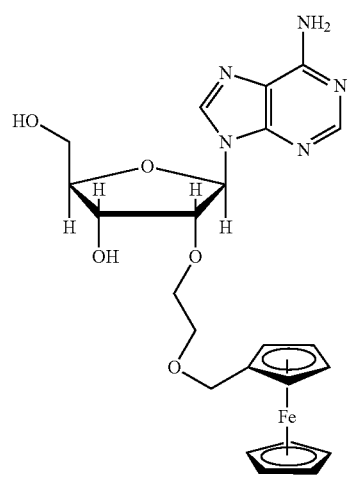

In an embodiment the compound of formula I is not any of

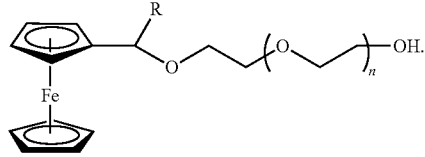

R = Me, n = 0 - 4 or 7
R = H, n = 2 or 3

In an embodiment of the compounds of the invention, Z is not —CH$_2$CH$_2$—. In an embodiment of the compounds of the invention, Y is not —CH(Me)-. In an embodiment X is not PPh$_2$.

EXAMPLES

Compounds of the invention can be prepared according to the procedures of the following schemes and examples, using appropriate materials. Moreover, by utilising the procedures described herein, one of ordinary skill in the art can readily prepare additional compounds that fall within the scope of the present invention. The reader will readily understand that known variations of the conditions and processes of the following preparative procedures can be used to prepare these compounds. Thus, the invention is not to be construed as being limited to the compounds illustrated in the examples.

The following abbreviations have been used in the examples:

| | |
|---|---|
| DMSO | Dimethylsulfoxide |
| THF | Tetrahydrofuran |
| DIPEA | N,N-diisopropylethylamine |
| PCR | polymerase chain reaction |
| pTSA | p-toluenesulfonic acid |
| Tf | trifluoromethanesulfonate |
| eq | equivalent(s) |
| TLC | thin layer chromatography |
| sat | saturated |
| HRMS | high resolution mass spectrometry |
| ESI | electrospray ionisation |

Compounds according to general formula I and II may be prepared using conventional synthetic methods, for example, but not limited to, the routes outlined in the schemes below. More detailed synthetic procedures can be found in the examples below.

Scheme 1

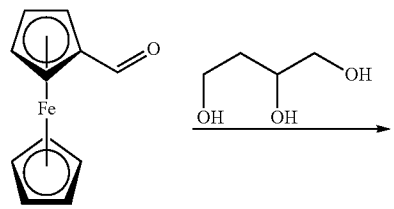

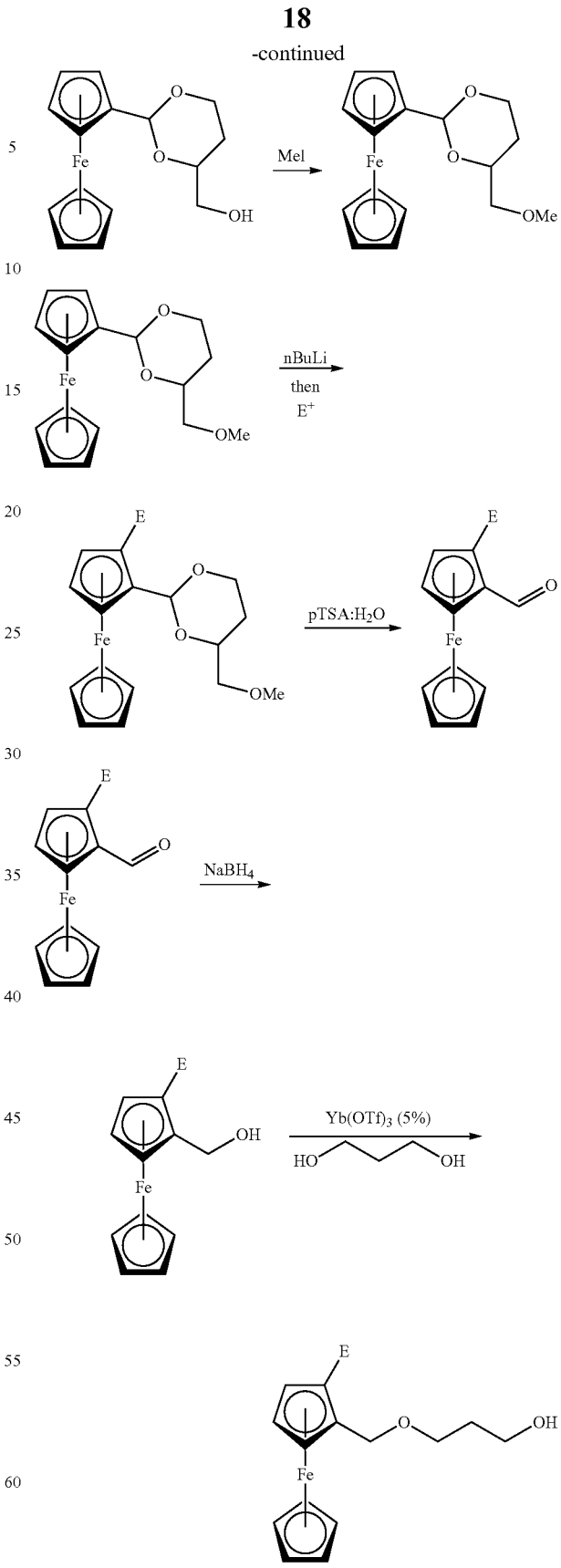

E$^+$ is any suitable electrophile useful for substituting a ferrocenyl group.

Scheme 2

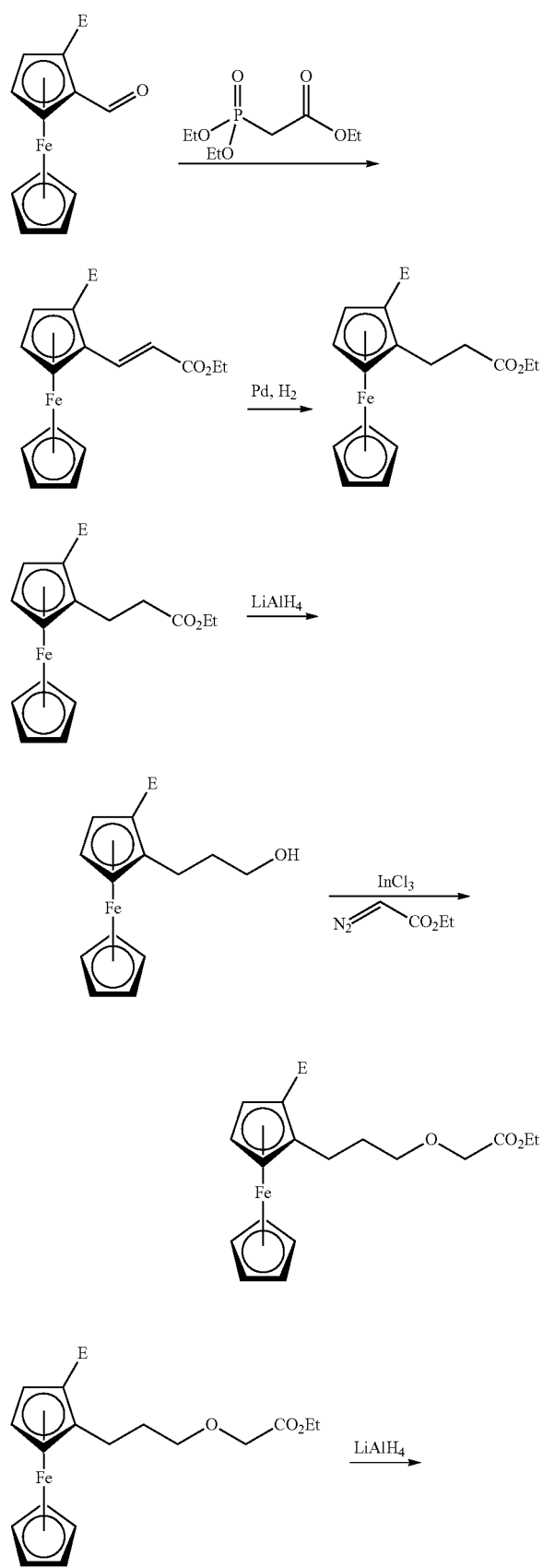

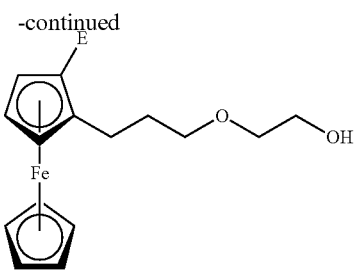

Scheme 3 illustrates the general synthetic procedure for attaching a phosphoramidite functional group to a linker hydroxyl group.

Scheme 3

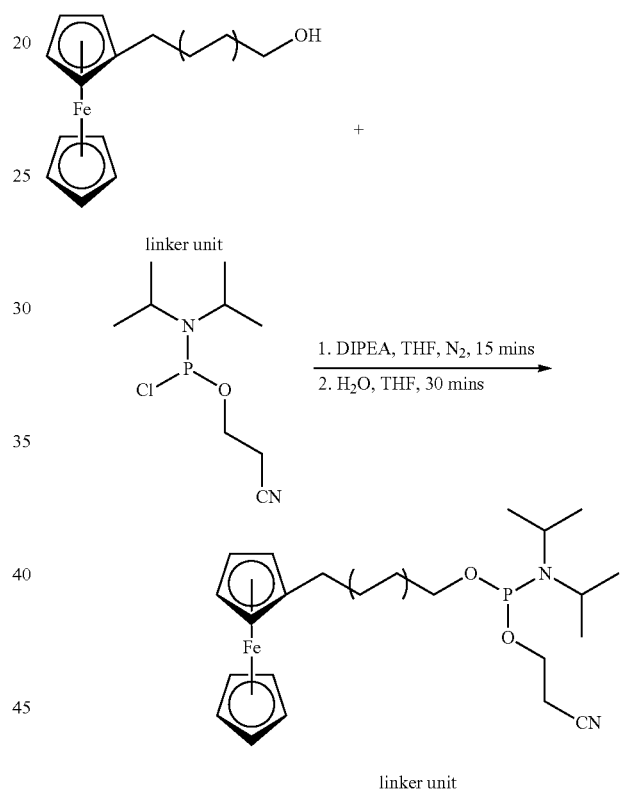

The ferrocenyl derivative shown as a starting material in the above reaction scheme is illustrative, and may be replaced by a molar equivalent of any of the compounds of the invention.

Determination of Electrochemical Potential

The electrochemical potential values mentioned hereafter were measured using an electrochemical cell including as background electrolyte an aqueous 100 mM solution of sodium chloride, using a printed carbon working electrode, a printed carbon counter electrode and a silver/silver chloride reference electrode, all with silver connectors. The electrodes were ink based and were screen printed on to a polymer substrate (for example Mylar®) followed by heat curing. By way of illustration, the sample may be prepared as follows: 0.01 M stock solution of the ferrocenyl compound is prepared in DMSO (1 cm$^3$). This is then further diluted to 14 µM in buffer. A 20 µL aliquot of this 14 µM solution is then applied to the screen printed electrode to run the electrochemical scan. An illustrative form of suitable cell is described and shown schematically in WO2012/085591.

Example 1: Preparation of 3-(ferrocenylmethoxy)propan-1ol (1)

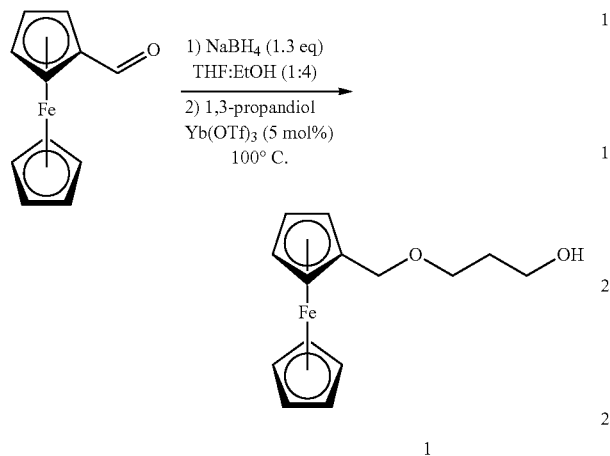

1

To a round bottomed flask equipped with a magnetic stirrer bar was added ferrocene carboxaldehyde (535 mg, 2.5 mmol, 1 eq). The flask was then charged with ethanol (4 cm$^3$) and THF (1 cm$^3$). The red solution was then treated with sodium borohydride (123 mg, 3.2 mmol, 1.3 eq). The flask was then sealed and placed under a nitrogen atmosphere. After 30 minutes the solution had changed colour to an orange and TLC analysis indicated full consumption of the starting material. The flask was then concentrated to ~90% of original volume in vacuo. The dark orange residue was then taken up in EtOAc (15 cm$^3$) and NaHCO$_3$ (15 cm$^3$). The bi-phasic mixture was transferred to separating funnel, the aqueous layer was separated and then back extracted with EtOAc (3×5 cm$^3$), the combined organic washings were then dried over MgSO$_4$, filtered and then concentrated in vacuo to give a yellow solid. The ferrocene methanol was then taken up in 1,3-propanediol (5 cm$^3$), the yellow solution was then treated with ytterbium (III) triflate (77 mg, 0.125 mmol, 5 mol %). The flask was then sealed and heated to 100° C. After heating for 10 minutes TLC analysis indicated full consumption of the starting material. The flask was cooled to room temperature, diluted with H$_2$O (20 cm$^3$) and EtOAc (20 cm$^3$). The organic layer was then separated and the aqueous layer back extracted with EtOAc (3×5 cm$^3$). The combined organic layers were then washed with H$_2$O (20 cm$^3$) and brine (sat) (20 cm$^3$) then dried over MgSO$_4$, filtered then concentrated in vacuo to give an orange solid. Purification was then carried out by silica-gel chromatography eluting with n-Hex 1:1 EtOAc to give the desired product 3-(ferrocenylmethoxy)propan-1ol (1) as an orange powder (514 mg, 74%).

$^1$H NMR (250 MHz, CDCl$_3$); $\delta_H$: 4.24 (s, 4H), 4.11 (s, 6H), 3.65 (t, 2H, J=5.4 Hz), 3.54 (t, 2H J=5.4 Hz), 3.65 (t, 2H J=5.4 Hz), 2.52 (br s, 1H), 1.7 (quin 2H, J=5.6 Hz); $^{13}$C NMR (75 MHz, CDCl$_3$); $\delta_C$: 83.6, 77.3, 71.5, 69.4, 69.3, 69.2, 68.7, 32.0; HRMS (ESI µTOF) calculated for C$_{14}$H$_{18}$FeO$_2$Na m/z 297.0553 found 297.0560 (m/z+Na$^+$); Electrochemical potential: 181 mV.

Example 2: Preparation of 3-(nonamethylferrocenylmethoxy)propan-1-ol (2)

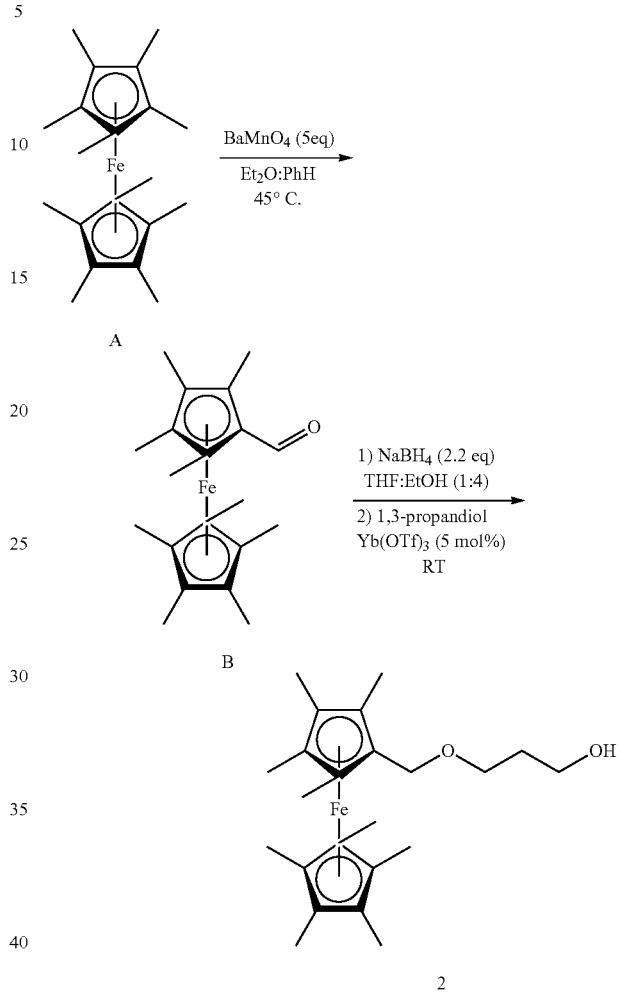

2

Nonamethylferrocene carboxaldehyde (B)

Decamethylferrocene (A) (4.80 g, 14.7 mmol) was placed in a round bottomed flask equipped with a magnetic stirrer bar. Fresh finely ground barium manganate (18.77 g, 73.6 mmol, 5 eq) was then added to the flask. The solids were then suspended in a mixture of dry benzene (20 cm$^3$) and dry diethyl ether (20 cm$^3$). The flask was then sealed and placed under a nitrogen atmosphere. The dark blue slurry was then sonicated for 45 mins. After this time the flask was removed from the sonicater and heated at 45° C. for 16 hours. After this time the dark slurry was filtered through a pad of celite and the solids washed with EtOAc (250 cm$^3$) until the washings ran clear. The red solution was then concentrated in vacuo to give a red solid. Purification by silica chromatography eluting with 5% EtOAc:nHex+2% TEA gave the product nonamethylferrocene carboxaldehyde (B) as a dark red crystalline solid (1.19 g, 23%).

$^1$H NMR (300 MHz, CDCl$_3$) $\delta_H$: 9.91 (s, 1H), 1.92 (s, 6H), 1.71 (s, 6H), 1.59 (s, 15H). $^{13}$C NMR (75 MHz, CDCl$_3$) $\delta_C$: 195.6, 86.0, 82.7, 80.6, 78.3, 72.5, 9.3, 9.3, 8.9. HRMS (ESI µTOF) calculated for C$_{20}$H$_{29}$FeO m/z 341.1484 found 341.1485 (m/z+H).

3-(Nonamethylferrocenylmethoxy)propan-1-ol (2)

The nonamethylferrocene carboxaldehyde (B) (3.43 g, 10.08 mmol, 1 eq) was placed in a round bottomed flask equipped with a magnetic stirrer bar. The flask then charged with ethanol (44 cm³) and 1,4-dioxane (11 cm³), the red solution was then treated with sodium borohydride (820 mg, 22.18 mmol, 2.2 eq). The flask was then sealed, placed under an argon atmosphere and stirred at room temperature for 16 hours. After this time TLC analysis indicated full consumption of the starting material. The orange solution was concentrated in vacuo to approximately 90% of original volume. The orange solid was then partitioned between H₂O (50 cm³) and CH₂Cl₂ (50 cm³). The organic layer was separated and the aqueous layer was back extracted with CH₂Cl₂ (3×15 cm³). The combined organics were then combined, washed with brine (sat) (50 cm³), dried over MgSO₄, filtered and concentrated in vacuo to give an orange solid. The crude alcohol was then suspended in 1,3-propanediol (50 cm³), CH₂Cl₂ (10 cm³) to give a red solution. The solution was then treated with ytterbium (III) triflate (334 mg, 0.54 mmol, 5 mol %). The flask was then sealed and placed under nitrogen atmosphere. After stirring for 30 mins at room temperature TLC analysis showed full consumption of the starting material. The reaction was then diluted with H₂O (150 cm³) and CH₂Cl₂ (100 cm³). The organic layer was separated and the aqueous layer extracted with CH₂Cl₂ (3×15 cm³). The combined organics were then washed with H₂O (3×50 cm³), dried over MgSO₄, filtered and concentrated in vacuo to give an orange oil. Purification by silica chromatography eluting with 10% EtOAc:nHex+2% TEA to give the desired product 3-(Nonamethylferrocenylmethoxy)propan-1-ol (2) as a yellow powder 3.16 g, 78%.

¹H NMR (300 MHz, C₆D₆) δ$_H$: 4.31 (s, 2H), 3.71 (s, 2H), 3.52 (t, 2H, J=5.7 Hz), 2.18 (s, 2H), 1.85 (s, 6H), 1.70 (s, 22H); ¹³C NMR (75 MHz, CDCl₃); δ$_C$: 83.6, 77.3, 71.5, 69.4, 69.3, 69.2, 68.7, 32.0; HRMS (ESI μTOF) calculated for C₂₃H₃₆FeO₂Na m/z 423.1962 found 423.1955 (m/z+Na⁺); Electrochemical potential: −151 mV.

Example 3: Preparation of 3-((1'-chloro)-ferrocenylmethoxy)propan-1-ol (3)

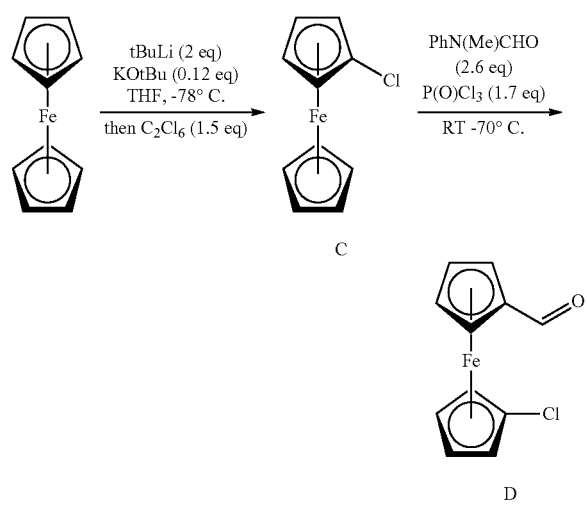

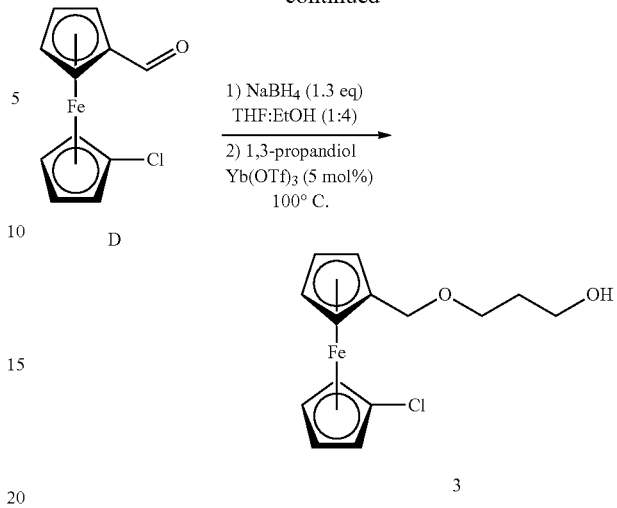

Chloroferrocene (C) was prepared from ferrocene using a modified procedure from *J. Organomet. Chem.*, 1996, 512, 219-224, using hexachloroethane as chlorinating reagent.

1'-Chloroferrocenecarboxaldehyde (D) was prepared from chloroferrocene, using the procedure from *Coll. Chechoslovak. Chemm. Commun.*, 1987, 52, 174-181, as a 4:1 mixture of the desired regioisomer.

The 1'-chloroferrocenecarboxaldehyde (D) (426 mg, 1.7 mmol, 1 eq) was placed in a round bottomed flask equipped with magnetic stirrer bar and dissolved in ethanol (4 cm³) and THF (1 cm³). The red solution was then treated with sodium borohydride (83 mg, 2.2 mmol, 1.3 eq), the flask was sealed and placed under a nitrogen atmosphere. After 30 mins the solution had turned orange in colour and TLC analysis indicated full consumption of the starting material. The flask was then concentrated to ~90% of original volume in vacuo. The dark orange residue was then taken up in EtOAc (15 cm³) and NaHCO₃ (sat) (15 cm³). The bi-phasic mixture was transferred to a separating funnel, the aqueous layer was separated and then back extracted with EtOAc (3×5 cm³). The combined organic washings were then combined dried over MgSO₄, filtered and then concentrated in vacuo to give an orange/yellow oil. The ferrocene methanol was then taken up in 1,3-propanediol (3 cm³), the yellow solution was then treated with ytterbium (III) triflate (56 mg, 0.09 mmol, 5 mol %). The flask was then sealed and heated to 100° C., after heated for 10 minutes TLC analysis indicated full consumption of the the starting material. The flask was cooled to room temperature, diluted with H₂O (10 cm³) and EtOAc (10 cm³). The organic layer was then separated and the aqueous layer back extracted with EtOAc (3×5 cm³). The combined organic layers were then washed with H₂O (20 cm³) and brine (sat) (20 cm³), dried over MgSO₄, filtered, then concentrated in vacuo to give a brown oil. Purification was then carried out by silica-gel chromatography eluting with 25% EtOAc:nHex to give the desired product 3-((1'-chloro)-ferrocenylmethoxy)propan-1-ol (3) as an orange oil (297 mg, 57%) as a 4:1 mixture of regioisomers.

¹H NMR (300 MHz, C₆D₆) δ$_H$(major) 4.26 (t, J=1.9 Hz, 2H), 4.19-4.13 (m, 4H), 4.03 (t, J=1.9 Hz, 2H), 3.78 (t, J=1.9 Hz, 2H), 3.69 (s, 2H), 3.46 (t, J=5.8 Hz, 2H), 1.73-1.65 (m, 2H); ¹³C NMR (75 MHz, C₆D₆) δ$_C$ (major) 93.3, 86.2, 71.5, 71.0, 69.6, 69.3, 69.0, 67.2, 62.0, 33.1; HRMS (ESI μTOF) calculated for C₁₄H₁₇ClFeO₂Na m/z 331.0164 found 331.0144 (m/z+Na⁺); Electrochemical potential: 352 mV.

Example 4: Preparation of 3-((2-tert-butylthio)-ferrocenylmethoxy)propan-1-ol (4)

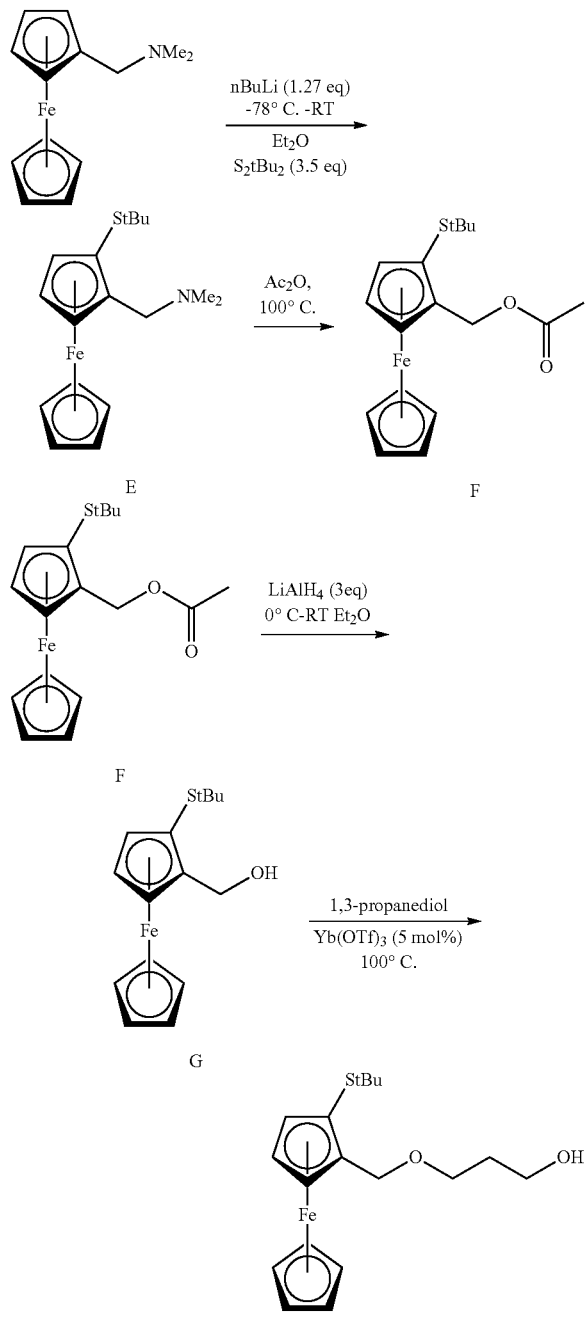

1-[(Dimethylamino)methyl]-2-(t-butylthio)-ferrocene (E) was prepared using the procedure from *Organomet.*, 1988, 7, 1297-1302.

1-[(Acetoxy)methyl]-2-(tert-butylthio)-ferrocene (F)

1-[(Dimethylamino)methyl]-2-(t-butylthio)-ferrocene (E) (1.21 g, 3.49 mmol) was dissolved in acetic anhydride (10 cm$^3$). The brown solution was then refluxed for 1 hour; TLC at this time indicated full consumption of the starting material. The solution was allowed to cool to room temperature, the solution was then concentrated in vacuo to approximately 90% of original volume. The resulting brown oil was then taken up in EtOAc (25 cm$^3$) and washed with NaHCO$_3$ (sat) (20 cm$^3$) and brine (sat) (20 cm$^3$). The brown solution was then dried over MgSO$_4$, filtered and concentrated in vacuo to give 1-[(acetoxy)methyl]-2-(tert-butylthio)-ferrocene (F) as an orange/brown oil (1.12 g, 93%) without need for further purification.

$^1$H NMR (250 MHz, C$_6$D$_6$) $\delta_H$ 5.37 (d, J=1.43 Hz, 2H), 4.51 (dd, J=2.6, 1.4 Hz, 1H), 4.44 (dd, J=2.6, 1.4 Hz, 1H), 4.07 (t, J=2.6 Hz, 1H), 4.07 (s, 5H) 1.82 (s, 3H), 1.33 (s, 9H).

2-tert-butylthio Ferrocene Methanol (G)

To a suspension of lithium aluminium hydride (369 mg, 9.71 mmol) in Et$_2$O (15 cm$^3$) at 0° C. was added 1-[(Acetoxy)methyl]-2-(tert-butylthio)-ferrocene (F) (1.12 g, 3.23 mmol) dropwise via syringe. Once addition was complete the slurry was allowed to warm to room temperature and stir for 30 mins. After this time the flask was cooled to 0° C. and then quenched by sequential addition of H$_2$O (369 μl), followed by 15% NaOH (aq) (369 μl) and H$_2$O (1.1 cm$^3$). The suspension was then allowed to warm to room temperature stirred for 10 minutes, filtered and concentrated in vacuo to give 2-tert-butylthio ferrocene methanol (G) as an orange solid (790 mg, 80%) without the need for further purification.

$^1$H NMR (250 MHz, C$_6$D$_6$) $\delta_H$ 4.64 (s, 2H), 4.41 (dd, J=2.4, 1.5 Hz, 1H), 4.32 (dd, J=2.4, 1.5 Hz, 1H), 4.17 (s, 5H), 4.08 (t, J=2.6 Hz, 1H), 1.28 (s, 9H). 3-((2-tert-butylthio)-ferrocenylmethoxy)propan-1-ol (4).

The 2-tert-butylthio ferrocene methanol (G) (778 mg, 2.5 mmol) was placed in a round bottomed flask equipped with a magnetic stirrer bar, and then suspended in 1,3-propandiol (10 cm$^3$). The yellow suspension was then treated with ytterbium (III) triflate (79 mg, 0.125 mmol, 5 mol %), the flask sealed, placed under a nitrogen atmosphere then heated to 100° C. After 10 mins TLC analysis indicated full consumption of the starting material. The brown solution was allowed to cool to room temperature, then diluted with H$_2$O (20 cm$^3$) and EtOAc (20 cm$^3$). The organic layer was separated and the aqueous layer back extracted with EtOAc (3×10 cm$^3$). The combined organics were washed with brine (sat) (2×10 cm$^3$), dried over MgSO$_4$, filtered and concentrated in vacuo to give an orange oil. Purification by silica chromatography eluting with 20% EtOAc:n-Hex to give the desired product 3-((2-tert-butylthio)-ferrocenylmethoxy)propan-1-ol (4) as an orange oil (899 mg, 99%).

$^1$H NMR (300 MHz, C$_6$D$_6$) $\delta_H$ 4.55 (d, J=10.7 Hz, 1H), 4.42 (dd, J=2.5, 1.4 Hz, 1H), 4.40 (dd, J=2.6, 1.6, 1H), 4.32 (d, J=10.7 Hz, 1H), 4.14 (s, 5H), 4.09 (t, J=2.6 Hz, 1H), 3.73 (q, J=5.8 Hz, 2H), 3.57 (qt, J=9.0, 5.8 Hz, 2H), 2.10 (t, J=5.8 Hz, 1H), 1.74 (p, J=5.8 Hz, 2H), 1.32 (s, 9H). $^{13}$C NMR (75 MHz, C$_6$D$_6$) $\delta_C$ 88.6, 77.7, 77.5, 71.0, 70.7, 70.2, 69.5, 68.4, 62.0, 45.7, 33.2, 31.4; HRMS (ESI μTOF) calculated for C$_{18}$H$_{26}$FeO$_2$SNa m/z 385.0918 found 385.0900 (m/z+Na$^+$); Electrochemical potential: 352 mV.

Example 5: Preparation of 3-((2-tert-butylsulfinyl)-ferrocenylmethoxy)propan-1-ol (5)

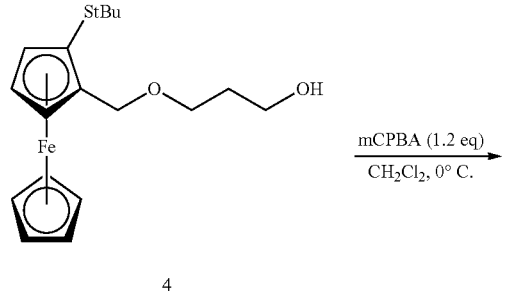

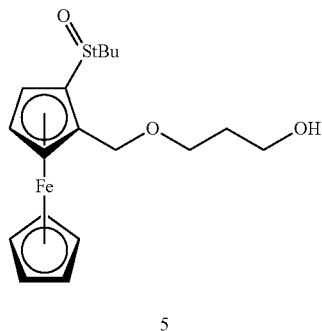

The 3-((2-tert-butylthio)-ferrocenylmethoxy)propan-1-ol (4) (459 mg, 1.2 mmol, 1 eq) was dissolved in CH$_2$Cl$_2$ (10 cm$^3$), the flask was then placed under a nitrogen atmosphere and cooled to 0° C. Once cold 3-chloro-perbenzoic acid (258 mg, 1.5 mmol, 1.2 eq) was added in one portion. The solution was then stirred at 0° C. for 15 minutes. After this time TLC analysis indicated full consumption of the starting material. The reaction was then quenched by addition of NaHCO$_3$ (sat) (15 cm$^3$) and stirred vigorously for 5 minutes. After this time the organic layer was separated and aqueous layer extracted with CH$_2$Cl$_2$ (3×5 cm$^3$). The combined organic were then washed with brine (sat) (10 cm$^3$), dried over MgSO$_4$, filter and concentrated in vacuo to give a dark brown oil. Purification by silica chromatography eluting with EtOAc gave the desired product 3-((2-tert-butylsulfinyl)-ferrocenylmethoxy)propan-1-ol (5) as orange amorphous solid (349 mg, 77%).

$^1$H NMR (300 MHz, C$_6$D$_6$) δ$_H$ 4.82 (dd, J=2.6, 1.5 Hz, 1H), 4.38 (s, 5H), 4.34-4.22 (m, 2H), 4.18 (d, J=11.1 Hz, 1H), 4.11 (t, J=2.6 Hz, 1H), 3.77 (q, J=5.5 Hz, 2H), 3.55 (ddd, J=9.0, 5.5, 5.5, Hz, 1H), 3.46 (ddd, J=9.0, 5.5, 5.5 Hz, 1H), 2.59 (t, J=5.5 Hz, 1H), 1.79 (p, J=5.5 Hz, 2H), 1.19 (s, 8H); $^{13}$C NMR (75 MHz, C$_6$D$_6$) δ$_C$ 88.7, 87.1, 72.0, 71.4, 69.7, 69.4, 68.0, 66.9, 61.1, 55.8, 33.4, 23.4; HRMS (ESI μTOF) calculated for C$_{18}$H$_{26}$FeO$_3$SNa m/z 401.08497 found 401.0838 (m/z+Na$^+$); Electrochemical potential: 474 mV.

Example 6: Preparation of 3-((2-tert-butylsulfonyl)-ferrocenylmethoxy)propan-1-ol (6)

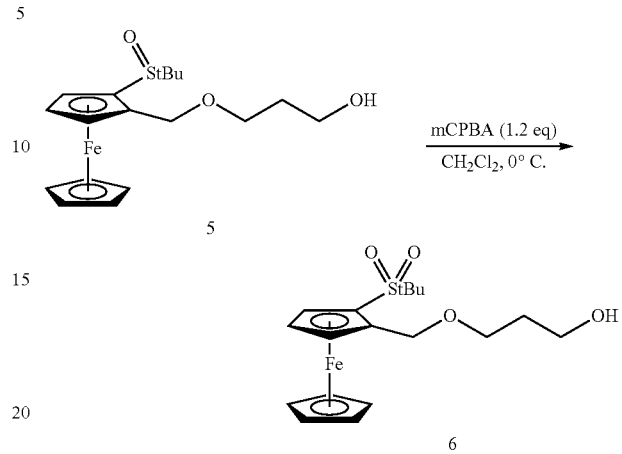

The 3-((2-tert-butylsulfinyl)-ferrocenylmethoxy)propan-1-ol (5) (349 mg, 0.92 mmol, 1 eq) was dissolved in CH$_2$Cl$_2$ (10 cm$^3$), the flask was then placed under a nitrogen atmosphere and cooled to 0° C. Once cold, 3-chloro-perbenzoic acid (190 mg, 1.1 mmol, 1.2 eq) was added in one portion. The solution was then stirred at 0° C. for 30 minutes. After this time TLC analysis indicated full consumption of the starting material. The reaction was then quenched by addition of NaHCO$_3$ (sat) (15 cm$^3$) and stirred vigorously for 5 minutes. After this time the organic layer was separated and aqueous layer extracted with CH$_2$Cl$_2$ (3×5 cm$^3$). The combined organic were then washed with brine (sat) (10 cm$^3$), dried over MgSO$_4$, filter and concentrated in vacuo to give a dark brown oil. Purification by silica chromatography eluting with 40% EtOAc:n-Hex gave the desired product 3-((2-tert-butylsulfonyl)-ferrocenylmethoxy)propan-1-ol (6) as a yellow solid (256 mg, 70%).

$^1$H NMR (300 MHz, C$_6$D$_6$) δ$_H$ 4.77 (d, J=11.0 Hz, 1H), 4.58 (dd, J=2.5, 1.6 Hz, 1H), 4.46 (d, J=11.0 Hz, 1H), 4.40 (s, 5H), 4.36 (dd, J=2.5, 1.6 Hz, 1H), 4.03 (t, J=2.5 Hz, 1H), 3.71 (t, J=5.8 Hz, 2H), 3.61-3.50 (m, 2H), 2.05 (s, 1H), 1.77-1.68 (m, 2H), 1.27 (s, 9H); $^{13}$C NMR (75 MHz, C$_6$D$_6$) δ$_C$ 86.7, 82.9, 73.7, 73.2, 72.1, 70.4, 70.1, 67.5, 61.7, 59.2, 33.2, 23.9; HRMS (ESI μTOF) calculated for C$_{18}$H$_{27}$FeO$_4$SNa m/z 418.0833 found 418.0824 (m/z+H); Electrochemical potential: 584 mV.

Example 7: Preparation of 3-((2-di-tert-butylphosphinyl)-ferrocenylmethoxy)propan-1-ol (7)

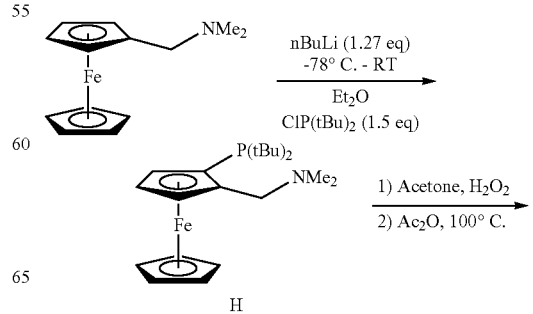

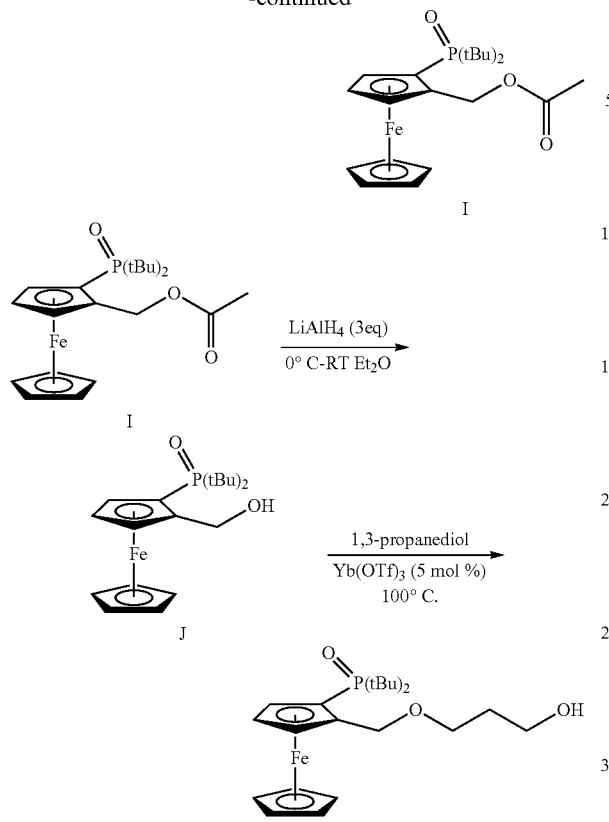

The 1-[(dimethylamino)methyl]-2-(t-di-tert-butylphoshonyl)-ferrocene (H) (4.82 g, 12.5 mmol, 1 eq) was placed in a round bottomed flask with a magnetic stirrer bar, and dissolved in acetone (30 cm³).

The orange solution was then cooled to 0° C. Once cold the solution was treated with H₂O₂ (50% wt) (812 µl, 14.3 mmol, 1.15 eq) dropwise over a 2 minute period. Once addition was complete the flask was allowed to warm to room temperature, after stirring for 15 minutes the reaction was complete. The flask was re-cooled to 0° C. and then quenched by addition of Na₂S₂O₃ (sat) (30 cm³). The solution was further diluted with EtOAc (50 cm³), the organic layer was separated and the aqueous layer back extracted with EtOAc (3×30 cm³). The combined organics were then washed with brine (sat) (30 cm³), dried over MgSO₄, filtered and concentrated in vacuo to give a thick red oil. This red oil was taken up in acetic anhydride (30 cm³), then heated at 100° C. for 2 hours. After this time the solution was allowed to cool to room temperature, the brown solution was then concentrated to approximately 90% of original volume. The resulting brown oil was then taken up in EtOAc (50 cm³). The solution was then washed with 2M NaOH (20 cm³), H₂O (2×20 cm³) and brine (sat) (50 cm³). The organic layer was then dried over MgSO₄, filtered and then concentrated in vacuo to give a brown oil. Purification by basic alumina chromatography, eluting with EtOAc gave the desired product 1-[(acetoxy)methyl]-2-(di-tert-butylphosphinyl)-ferrocene (I) as a red oil (2.30 g, 44%). ¹H NMR (300 MHz, C₆D₆) δ$_H$ 5.87 (d, J=12.3 Hz, 1H), 5.62 (d, J=12.3 Hz, 1H), 4.58-4.47 (m, 1H), 4.19-4.06 (m, 6H), 3.80 (brs, 1H), 1.85 (s, 3H), 1.48 (d, J$^{P-H}$=16.7 Hz, 9H), 1.21 (d, J$^{P-H}$=16.7 Hz, 9H); ³¹P{H} NMR (122 MHz, C₆D₆) δ$_P$ 58.59; ¹³C NMR (75 MHz, C₆D₆) δ$_C$ 170.5, 72.5, 71.3, 62.4, 60.4, 42.2, 41.4, 38.0, 37.3, 37.2, 36.5, 27.7, 27.0, 26.9, 21.1, 14.6; HRMS (ESI µTOF) calculated for C₂₁H₃₁FeO₃PNa m/z 441.1257 found 441.1265 (m/z+Na⁺).

2-(di-tert-Butyl-phosphinyl)-ferrocene Methanol (J)

To a suspension of lithium aluminium hydride (628 mg, 16.5 mmol, 3 eq) in dry diethyl ether (10 cm³) under nitrogen at 0° C., was added the 2-di-tert-butylphosphinyl-acetoxy methyl ferrocene (I) (2.30 g, 5.5 mmol, 1 eq) in dry diethyl ether (10 cm³) dropwise via syringe over a 2 minute period. Once addition was complete the flask was then refluxed overnight. After this time the flask was then cooled to 0° C. and the reaction was then quenched by sequential addition of H₂O (628 µl), 15% NaOH (aq) (628 µl) and H₂O (1.88 cm³). The orange slurry was then allowed to stir at room temperature for 10 mins. The solids were then removed by filtration and then washed with Et₂O until washings ran clear. The orange solution was then concentrated in vacuo to give the desired product 2-(di-tert-Butyl-phosphinyl)-ferrocene methanol (J) as an orange powder (2.03 g, 99%) without the need for further purification. ¹H NMR (300 MHz, C₆D₆) δ$_H$ 6.84 (brs, 1H), 4.69 (dd, J=13.0, 3.4 Hz, 1H), 4.49 (dd, J=13.0, 8.4 Hz, 1H), 4.23 (s, 5H), 4.19-4.13 (m, 1H), 4.04 (dd, J=4.3, 2.3 Hz, 1H), 3.77 (brs, 1H), 1.45 (d, J=13.8 Hz, 10H), 0.99 (d, J=13.8 Hz, 9H); ³¹P{¹H} NMR (122 MHz, C₆D₆) δ$_P$ 62.27; ¹³C NMR (75 MHz, C₆D₆) δ$_C$ 98.3, 72.7, 72.6, 72.5, 72.3, 71.3, 70.2, 70.1, 60.7, 38.2, 37.3, 36.9, 36.1, 27.2, 26.7; HRMS (ESI µTOF) calculated for C₁₉₃₀₉FeO₂P m/z 377.2349 found 377.2301 (m/z+H).

3-((2-di-tert-butylphosphinyl)-ferrocenylmethoxy) propan-1-ol (7)

The 2-di-tert-butyl-phosphinyl-ferrocene methanol (J) (376 mg, 1 mmol, 1 eq) was suspended in 1,3-propane-diol (5 cm³). The suspension was treated with ytterbium (III) triflate (31 mg, 0.05 mmol, 5 mol %). The flask was sealed and then heated at 100° C. for 15 mins. The flask was allowed to cool to room temperature and the solution was diluted with H₂O (15 cm³) and EtOAc (30 cm³). The organic layer was separated and the aqueous layer back extracted with EtOAc (3×5 cm³). The combined organics were then washed with H₂O (3×5 cm³) and brine (sat) (10 cm³). The combined organics were then dried over MgSO₄, filtered and concentrated in vacuo to give a brown oil. Purification by basic alumina chromatography eluting with EtOAc gave the desired product 3-((2-di-tert-butylphospinyl)-ferrocenylmethoxy)propan-1l-ol (7) as an orange oil (157 mg, 36%). ¹H NMR (300 MHz, C₆D₆) δ$_H$ 5.47 (brs, 1H), 4.77 (d, J=10.7 Hz, 1H), 4.6-4.52 (m, 2H), 4.21-4.13 (m, 7H), 4.03-3.84 (m, 3H), 3.81 (brs, 1H), 2.09-1.95 (m, 2H), 1.47 (d, J=13.6 Hz, 9H), 1.05 (d, J=13.6 Hz, 9H); ³¹P{H} NMR (122 MHz, C₆D₆) δ$_H$ 60.53. ¹³C NMR (75 MHz, C₆D₆) δ$_H$ 92.2, 72.9, 72.8, 72.4, 72.2, 72.2, 71.4, 71.3, 71.0, 71.0, 70.9, 69.1, 68.8, 59.4, 38.1, 37.3, 37.1, 36.3, 33.8, 27.5, 27.1; HRMS (ESI µTOF) calculated for C₂₂H₃₅FeO₃PNa m/z 457.1639 found 457.1626 (m/z+Na⁺); Electrochemical potential: 419 mV.

Example 8: Preparation of 3-(2-tributylstannyl-ferrocenylmethoxy)propan-1-ol (8)

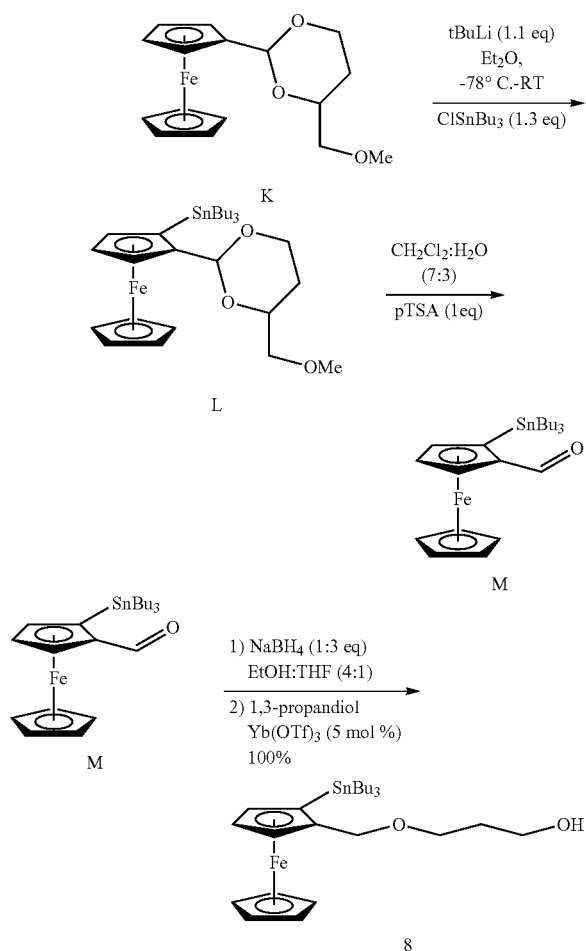

(rac)-4-(Methoxymethyl)-2-ferrocenyl-1,3-dioxane (K), (rac)-4-(Methoxymethyl)-2-(α-(tributylstannyl)-ferrocenyl)-1,3-dioxane (L) and 2-tributylstannyl ferrocene carboxaldehyde (M) were prepared according to the procedures in *J. Org. Chem.*, 1997, 62, 6733-6745.

2-Tributylstannyl ferrocene carboxaldehyde (M) (447 mg, 0.88 mmol, 1 eq) was dissolved in EtOH:THF mixture (4:1) (5 cm$^3$). The red solution was then treated with sodium borohydride (42 mg, 1.1 mmol, 1.3 eq) and the red solution was then stirred at room temperature for 1 hour. After this time the now orange solution was treated with H$_2$O (10 cm$^3$) and diluted with EtOAc (10 cm$^3$). The organic layer was separated and the aqueous layer back extracted with EtOAc (3×5 cm$^3$). The combined organics were then washed with brine (sat) (10 cm$^3$), dried over MgSO$_4$, filtered and concentrated in vacuo to give the desired alcohol as an orange oil. The oil was suspended in 1,3-propanediol (3 cm$^3$), then treated with ytterbium (III) triflate (27 mg, 0.044 mmol, 5 mol %). The flask was sealed, then heated to 100° C. for 10 minutes. The flask was then cooled to room temperature and the solution was diluted with H$_2$O (10 cm$^3$) and EtOAc (10 cm$^3$). The organic layer was separated and the aqueous layer was back extracted with EtOAc (3×5 cm$^3$). The combined organics were then washed with brine (sat) (25 cm$^3$), dried over MgSO$_4$, filtered and concentrated in vacuo to give an orange oil. Purification by silica chromatography eluting with 20% EtOAc:n-Hex gave the desired product 3-(2-tributylstannyl-ferrocenylmethoxy)propan-1-ol (8) as an orange oil (280 mg, 57%)

$^1$H NMR (300 MHz, C$_6$D$_6$) δ$_H$ 4.43-4.33 (m, 2H), 4.28 (t, J=2.3 Hz, 1H), 4.18-4.09 (m, 7H), 3.70 (q, J=5.6 Hz, 2H), 3.58 (ddd, J=9.1, 5.6, 5.5 Hz, 1H), 3.49 (ddd, J=9.1, 5.6, 5.5 Hz, 1H), 1.81-1.73 (m, 6H), 1.63-1.46 (m, 6H), 1.31-1.25 (m 8H), 1.07 (t, J=7.3 Hz, 9H); $^{13}$C NMR (75 MHz, C$_6$D$_6$) δ$_H$ 89.9, 76.1, 72.7, 71.4, 71.2, 69.4, 69.2, 61.9, 33.1, 30.1, 28.3, 14.3, 11.2; $^{115}$Sn{$^1$H} NMR (112 MHz, C$_6$D$_6$) δ$_{Sn}$ −20.71. HRMS (ESI µTOF) calculated for C$_{26}$H$_{44}$FeO$_2$SnNa m/z 587.1610 found 587.1607 (m/z+Na$^+$); Electrochemical potential: 303 mV.

Example 9: Preparation of 3-(2-trimethylsilyl-ferrocenylmethoxy)propan-1-ol (9)

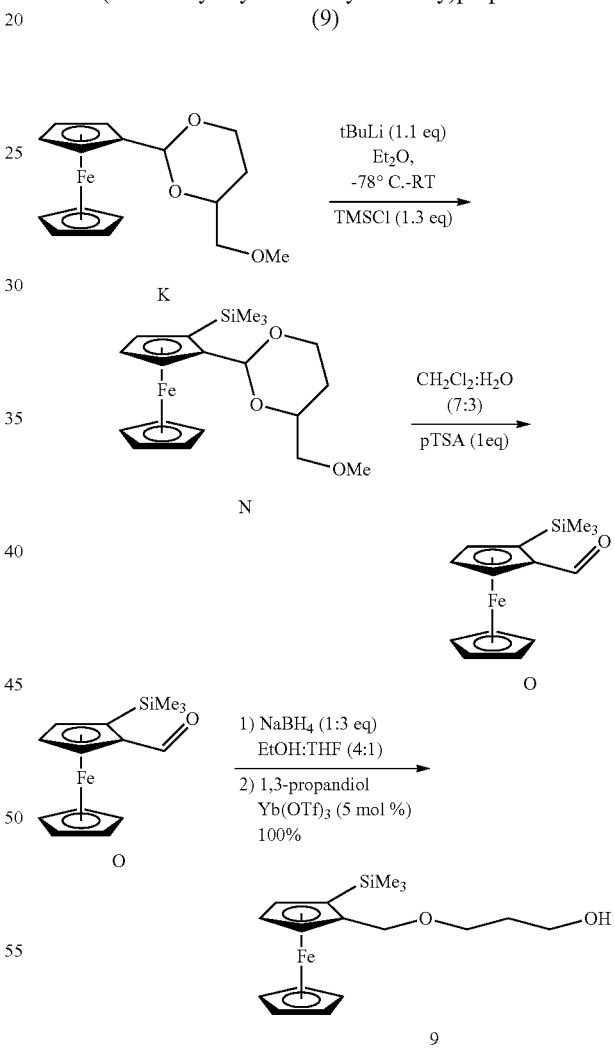

(rac)-4-(Methoxymethyl)-2-ferrocenyl-1,3-dioxane (K), (rac)-4-(Methoxymethyl)-2-(α-(trimethylsilyl)-ferrocenyl)-1,3-dioxane (N) and 2-trimethylsilyl ferrocene carboxaldehyde (O) were prepared according to the procedures in *J. Org. Chem.*, 1997, 62, 6733-6745.

2-Trimethylsily ferrocene carboxaldehyde (O) (266 mg, 0.93 mmol, 1 eq) was dissolved in EtOH:THF mixture (4:1)

(5 cm³). The red solution was then treated with sodium borohydride (44 mg, 1.2 mmol, 1.3 eq) and then stirred at room temperature for 1 hour. After this time the now orange solution was treated with H₂O (10 cm³) and diluted with EtOAc (10 cm³). The organic layer was separated and the aqueous layer back extracted with EtOAc (3×5 cm³). The combined organics were then washed with brine (sat) (10 cm³), dried over MgSO₄, filtered and concentrated in vacuo to give the desired alcohol as an orange oil. The oil was suspended in 1,3-propanediol (3 cm³), then treated with ytterbium (III) triflate (28 mg, 0.046 mmol, 5 mol %). The flask was sealed then heated to 100° C. for 2 minutes. The flask was then cooled to room temperature, the solution was diluted with H₂O (10 cm³) and EtOAc (10 cm³). The organic layer was separated and the aqueous layer was back extracted with EtOAc (3×5 cm³). The combined organics were then washed with brine (sat) (25 cm³), dried over MgSO₄, filtered and concentrated in vacuo to give an orange oil. Purification by silica chromatography eluting with 20% EtOAc:n-Hex gave the desired product as an orange oil (124 mg, 38%).

$^1$H NMR (300 MHz, C₆D₆) δ$_H$ 4.29 (d, J=11.2 Hz, 1H), 4.15 (dd, J=2.3, 1.3 Hz, 1H), 4.05 (t, J=2.3 Hz, 1H), 3.94-3.88 (m, 7H), 3.54 (q, J=6.1 Hz, 2H), 3.41-3.26 (m, 2H) 1.67 (t, J=6.1 Hz, 1H), 1.62-1.51 (m, 2H), 0.28 (s, 9H); $^{13}$C NMR (75 MHz, C₆D₆) δ$_C$ 88.2, 74.7, 73.0, 71.6, 69.8, 69.3, 68.4, 68.3, 61.0, 32.3, 0.0; HRMS (ESI μTOF) calculated for C₁₇H₂₆FeO₂SiNa m/z 369.0949 found 369.0954 (m/z+Na⁺); Electrochemical potential: 248 mV.

Example 10: Preparation of 3-(2-tributylsilyl-ferrocenylmethoxy)propan-1-ol (10)

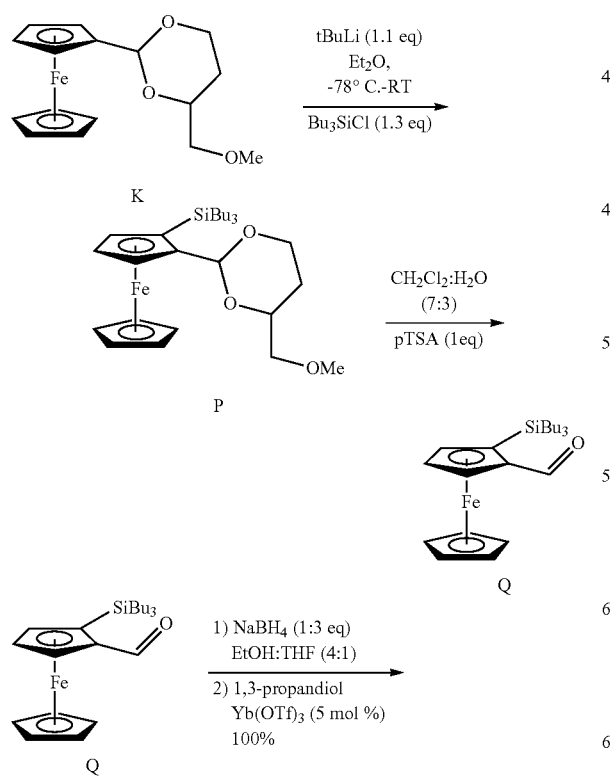

(rac)-4-(Methoxymethyl)-2-ferrocenyl-1,3-dioxane (K), was prepared according to the procedures in *J. Org. Chem.*, 1997, 62, 6733-6745.

(rac)-4-(Methoxymethyl)-2-(α-(tributylsilyl)-ferrocenyl)-1,3-dioxane (P) was prepared via the procedure in *J. Org. Chem.*, 1997, 62, 6733-6745 using tribuylsilychloride as the electrophile.

2-tributylsilyl ferrocene carboxaldehyde (Q) was prepared via adapting the procedure in *J. Org. Chem.*, 1997, 62, 6733-6745.

2-Tributylsilyl ferrocene carboxaldehyde (Q) (461 mg, 1.12 mmol, 1 eq) was dissolved in EtOH:THF mixture (4:1) (5 cm³). The red solution was then treated with sodium borohydride (55 mg, 1.46 mmol, 1.3 eq) and the red solution was then stirred at room temperature for 1 hour. After this time the now orange solution was treated with H₂O (10 cm³) and diluted with EtOAc (10 cm³). The organic layer was separated and the aqueous layer back extracted with EtOAc (3×5 cm³). The combined organics were then washed with brine (sat) (10 cm³), dried over MgSO₄, filtered and concentrated in vacuo to give the desired alcohol as an orange oil. The oil was suspended in 1,3-propanediol (3 cm³), then treated with ytterbium (III) triflate (35 mg, 0.056 mmol, 5 mol %). The flask was sealed then heated to 100° C. 20 minutes. The flask was then cooled to room temperature, the solution was diluted with H₂O (10 cm³) and EtOAc (10 cm³). The organic layer was separated and the aqueous layer was back extracted with EtOAc (3×5 cm³). The combined organics were then washed with brine (sat) (25 cm³), dried over MgSO₄, filtered and concentrated in vacuo to give an orange oil. Purification by silica chromatography eluting with 20% EtOAc:n-Hex gave the desired product 3-(2-tributylsilyl-ferrocenylmethoxy)propan-1-ol (10) as an orange oil (71 mg, 13%).

$^1$H NMR (300 MHz, C₆D₆) δ$_H$ 4.46 (d, J=11.0 Hz, 1H), 4.34 (dd, J=2.3, 1.2 Hz, 1H), 4.23 (t, J=2.3 Hz, 1H), 4.21-4.05 (m, 7H), 3.72 (q, J=5.5 Hz, 2H), 3.63-3.44 (m, 2H), 1.84 (t, J=5.4 Hz, 1H), 1.80-1.70 (m, 2H), 1.61-1.54 (m, 12H), 1.10-1.01 (m, 15H); $^{13}$C NMR (75 MHz, C₆D₆) δ$_C$ 88.8, 75.9, 73.7, 71.0, 70.9, 70.5, 69.5, 69.4, 61.9, 33.2, 27.7, 27.3, 14.5; HRMS (ESI μTOF) calculated for C₂₆H₄₄FeO₂NaSi m/z 495.2357 found 495.2381 (m/z+Na⁺); Electrochemical potential: 361 mV.

Example 11: Preparation of 3-(2-trimethylstannyl-ferrocenylmethoxy)propan-1-ol (11)

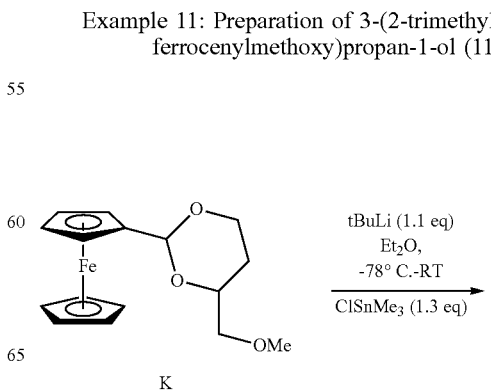

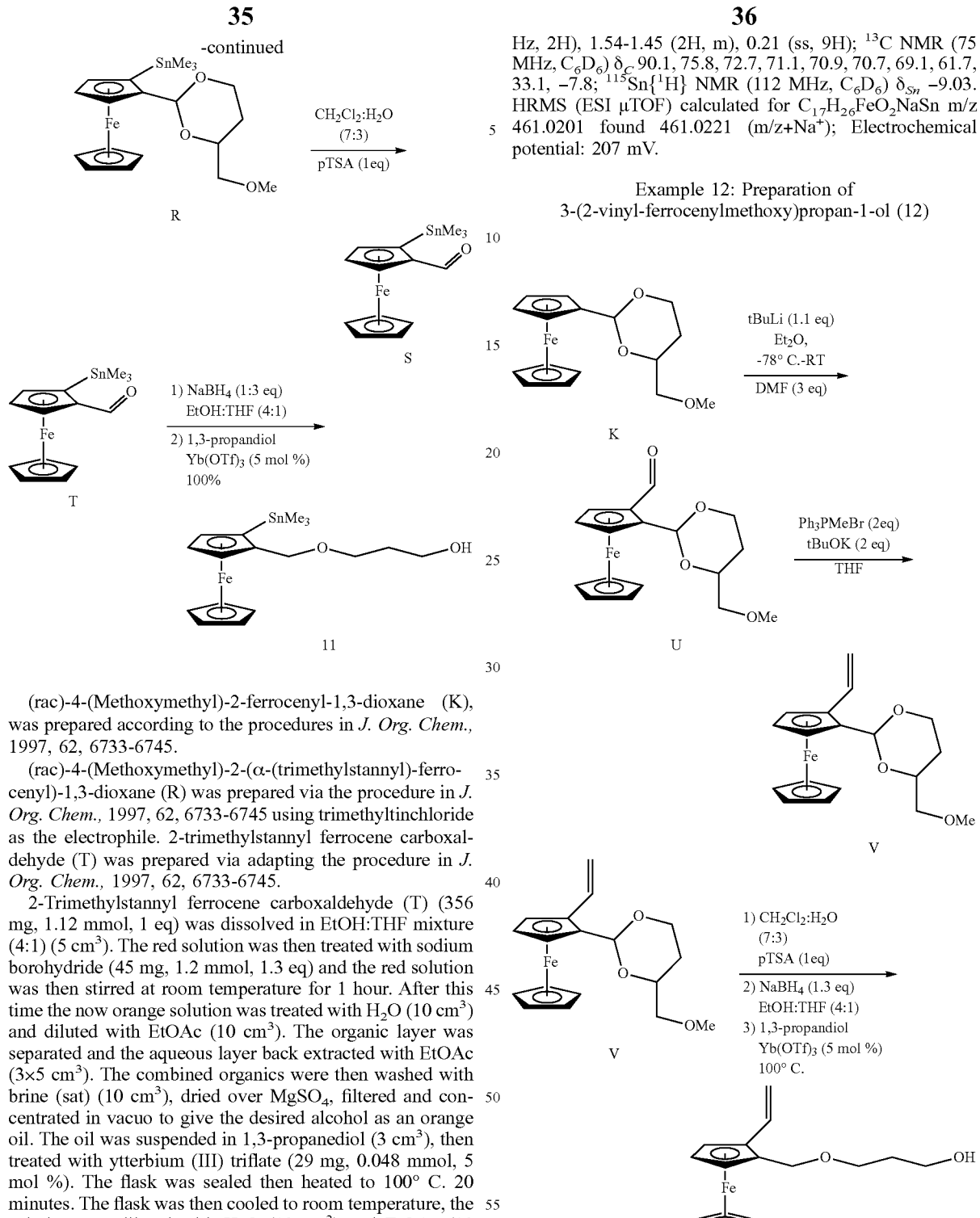

(rac)-4-(Methoxymethyl)-2-ferrocenyl-1,3-dioxane (K), was prepared according to the procedures in *J. Org. Chem.*, 1997, 62, 6733-6745.

(rac)-4-(Methoxymethyl)-2-(α-(trimethylstannyl)-ferrocenyl)-1,3-dioxane (R) was prepared via the procedure in *J. Org. Chem.*, 1997, 62, 6733-6745 using trimethyltinchloride as the electrophile. 2-trimethylstannyl ferrocene carboxaldehyde (T) was prepared via adapting the procedure in *J. Org. Chem.*, 1997, 62, 6733-6745.

2-Trimethylstannyl ferrocene carboxaldehyde (T) (356 mg, 1.12 mmol, 1 eq) was dissolved in EtOH:THF mixture (4:1) (5 cm$^3$). The red solution was then treated with sodium borohydride (45 mg, 1.2 mmol, 1.3 eq) and the red solution was then stirred at room temperature for 1 hour. After this time the now orange solution was treated with H$_2$O (10 cm$^3$) and diluted with EtOAc (10 cm$^3$). The organic layer was separated and the aqueous layer back extracted with EtOAc (3×5 cm$^3$). The combined organics were then washed with brine (sat) (10 cm$^3$), dried over MgSO$_4$, filtered and concentrated in vacuo to give the desired alcohol as an orange oil. The oil was suspended in 1,3-propanediol (3 cm$^3$), then treated with ytterbium (III) triflate (29 mg, 0.048 mmol, 5 mol %). The flask was sealed then heated to 100° C. 20 minutes. The flask was then cooled to room temperature, the solution was diluted with H$_2$O (10 cm$^3$) and EtOAc (10 cm$^3$). The organic layer was separated and the aqueous layer was back extracted with EtOAc (3×5 cm$^3$). The combined organics were then washed with brine (sat) (25 cm$^3$), dried over MgSO$_4$, filtered and concentrated in vacuo to give an orange oil. Purification by silica chromatography eluting with 20% EtOAc:n-Hex gave the desired product 3-(2-trimethylstannyl-ferrocenylmethoxy)propan-1-ol (11) as an orange oil (190 mg, 48%)

$^1$H NMR (300 MHz, C$_6$D$_6$) δ$_H$ 4.16-4.10 (m, 2H), 4.05 (t, J=2.3 Hz, 1H), 3.92-3.86 (m, 6H), 3.85 (dd, J=2.2, 1.1 Hz, 1H), 3.45 (dd, J=11.3, 5.6 Hz, 2H), 3.27 (ddt J=20.7, 9.1, 5.6 Hz, 2H), 1.54-1.45 (2H, m), 0.21 (ss, 9H); $^{13}$C NMR (75 MHz, C$_6$D$_6$) δ$_C$ 90.1, 75.8, 72.7, 71.1, 70.9, 70.7, 69.1, 61.7, 33.1, −7.8; $^{115}$Sn{$^1$H} NMR (112 MHz, C$_6$D$_6$) δ$_{Sn}$ −9.03. HRMS (ESI μTOF) calculated for C$_{17}$H$_{26}$FeO$_2$NaSn m/z 461.0201 found 461.0221 (m/z+Na$^+$); Electrochemical potential: 207 mV.

Example 12: Preparation of 3-(2-vinyl-ferrocenylmethoxy)propan-1-ol (12)

(rac)-4-(Methoxymethyl)-2-ferrocenyl-1,3-dioxane (K) and (rac)-4-(Methoxymethyl)-2-(α-formyl-ferrocenyl)-1,3-dioxane (U) were prepared according to the procedures in *J. Org. Chem.*, 1997, 62, 6733-6745.

(rac)-4-(Methoxymethyl)-2-(α-vinyl-ferrocenyl)-1,3-dioxane (V)

(rac)-4-(Methoxymethyl)-2-(α-formyl-ferrocenyl)-1,3-dioxane (U) (481 mg, 1.4 mmol, 1 eq) was dissolved in dry THF (15 cm³) and then treated with methyltriphenyl phosphonium bromide (999 mg, 2.8 mmol, 2 eq) and potassium tert-butoxide (313 mg, 2.8 mmol, 2 eq). The mixture was then stirred at room temperature for 3 hours. After this time the reaction was quenched by addition of H₂O (10 cm³). The organic layer was then separated and the aqueous layer back extracted with EtOAc (3×5 cm³). The combined organics were then dried over MgSO₄, filtered and concentrated in vacuo to give an orange oil. Purification by silica chromatography eluting with 20% EtOAc:n-Hex to give the desired product (rac)-4-(Methoxymethyl)-2-(α-vinyl-ferrocenyl)-1,3-dioxane (V) as an orange oil (137 mg, 29%).

$^1$H NMR (300 MHz, C₆D₆) $\delta_H$ 6.80 (dd, J=17.6, 10.9 Hz, 1H), 5.42 (dd, J=17.6, 1.8 Hz, 1H), 5.35 (s, 1H), 5.08 (dd, J=10.9, 1.8 Hz, 1H), 4.57 (dd, J=2.4, 1.5 Hz, 1H), 4.25 (dd, J=2.4, 1.5 Hz, 1H), 4.06 (s, 5H), 3.94 (t, J=2.4 Hz, 1H), 3.88 (ddd, J=11.5, 5.5, 1.2 Hz, 1H), 3.42 (ddd, J=10.1, 11.5, 2.6 Hz, 1H), 3.25 (dd, J=10.1, 5.5 Hz, 1H), 3.09-3.03 (m, 4H), 1.65-1.46 (m, 1H), 1.03-0.92 (m, 1H); $^{13}$C NMR (75 MHz, C₆D₆) $\delta_H$ 134.7, 112.4, 100.5, 85.4, 82.8, 76.7, 76.2, 70.8, 69.1, 68.1, 67.1, 66.90, 59.4, 28.8; HRMS (ESI TOF) calculated for C₁₈H₂₂FeO₃Na m/z 365.0816 found 365.0818 (m/z+Na⁺).

3-(2-Vinyl-ferrocenylmethoxy)propan-1-ol (12)

The (rac)-4-(methoxymethyl)-2-(α-vinyl-ferrocenyl)-1,3-dioxane (V) (137 mg, 0.4 mmol, 1 eq) was placed in a Schlenk tube with para-toluenesulfonic acid monohydrate (200 mg, 1 mmol, 2.5 eq). The flask was sealed then evacuated and back filled with argon four times. The flask was then charged with CH₂Cl₂ (7 cm³) and H₂O (3 cm³). The bi-phasic mixture was then stirred vigorously for 18 hours. After this time the organic layer was separated and the aqueous layer back extracted with CH₂Cl₂ (3×5 cm³). The combined organics were then washed with H₂O (10 cm³), then dried over MgSO₄, filtered and concentrated in vacuo to give the aldehyde as a red oil. This was then taken up in EtOH:THF (4:1) (5 cm³) and treated with sodium borohydride (27 mg, 0.48 mmol, 1.2 eq). The red solution was then stirred at room temperature for 30 minutes. At this point the orange solution was treated with NaHCO₃ (sat) (10 cm³) and then diluted with EtOAc (10 cm³). The organic layer was separated and the aqueous layer back extracted with EtOAc (3×5 cm³). The combined organics were then washed with H₂O (10 cm³), dried over MgSO₄, filtered and then concentrated in vacuo to give the target alcohol as an orange oil. This was then dissolved in 1,3-propandiol (3 cm³), the solution was treated with ytterbium (III) triflate (12 mg, 0.02 mmol, 5 mol %). The flask was sealed and then heated at 100° C. for 15 minutes. The flask was then allowed to cool to room temperature, the brown solution was then diluted with EtOAc (10 cm³) and H₂O (10 cm³). The organic layer was separated and the aqueous layer back extracted with EtOAc (3×5 cm³). The combined organics were washed with H₂O (25 cm³), dried over MgSO₄, filtered and concentrated in vacuo to give an orange oil. Purification by silica chromatography eluting with 40% EtOAc:n-Hex to give the desired product 3-(2-Vinyl-ferrocenylmethoxy)propan-1-ol (12) as an orange oil (3 mg, 2.5%).

$^1$H NMR (300 MHz, C₆D₆) $\delta_H$ 6.47 (dd, J=17.5, 10.9 Hz, 1H), 5.39 (dd, J=17.5, 1.7 Hz, 1H), 5.05 (dd, J=10.9, 1.7 Hz, 1H), 4.42-4.29 (m, 2H), 4.08-3.91 (m, 6H), 3.87 (s, 5H), 3.54 (dd, J=11.2, 5.5 Hz, 2H), 3.41-3.28 (m, 2H), 1.70 (t, J=5.4 Hz, 1H), 1.53 (dt, J=7.6, 5.8 Hz, 2H); $^{13}$C NMR (75 MHz, C₆D₆) $\delta_C$ 133.7, 112.7, 82.9, 82.3, 71.5, 70.3, 69.1, 68.4, 68.2, 67.1, 64.7, 61.9, 33.1; HRMS (ESI TOF) calculated for C₁₆H₂₀FeO₂Na m/z 323.0630 found 323.0646 (m/z+Na⁺); Electrochemical potential: 220 mV.

Example 13: Preparation of 3-(2-iodo-ferrocenylmethoxy)propan-1-ol (13)

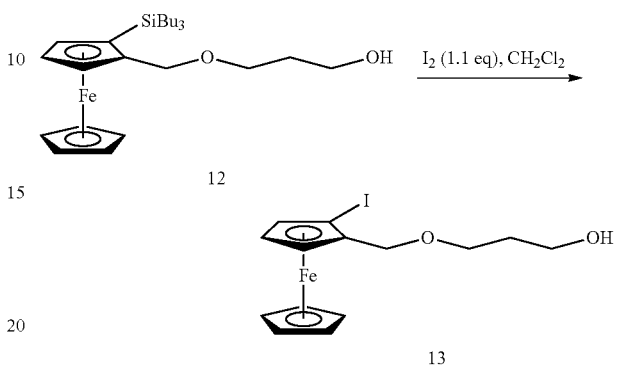

3-(2-tributylsilyl-ferrocenylmethoxy)propan-1-ol (12) (265 mg, 0.47 mmol, 1 eq) was dissolved in CH₂Cl₂ (2.5 cm³) and then treated with iodine (130 mg, 0.51 mmol, 1.1 eq). The dark brown solution was then stirred at room temperature for 16 hours. After this time the reaction was quenched by addition of sodium thiosulphate (sat) (5 cm³). The organic layer was separated and the aqueous layer back extracted with CH₂Cl₂ (3×5 cm³). The combined organics were then dried over MgSO₄, filtered and concentrated in vacuo to give an orange oil. Purification by silica chromatography eluting with 30% EtOAc:n-Hex to give the desired product 3-(2-iodo-ferrocenylmethoxy)propan-1-ol (13) as an orange oil (15 mg, 8%).

$^1$H NMR (300 MHz, C₆D₆) $\delta_H$ 4.36-4.28 (m, 2H), 4.19 (d, J=11.5 Hz, 1H), 4.14 (dd, J=2.5, 1.3 Hz, 1H), 4.01 (s, 5H), 3.91 (t, J=2.5 Hz, 1H), 3.71 (dd, J=10.6, 5.3 Hz, 2H), 3.61-3.47 (m, 2H), 1.76-1.65 (m, 2H); $^{13}$C NMR (75 MHz, C₆D₆) 5c 85.8, 75.6, 72.1, 69.7, 69.7, 69.6, 68.9, 61.9, 45.3, 33.1, 32.3, 23.4, 14.7; HRMS (ESI TOF) calculated for C₁₄H₁₇FeO₂INa m/z 422.9520 found 422.9538 (m/z+Na⁺); Electrochemical potential: 355 mV.

Example 14: Preparation of 2-(3-ferrocenylpropoxy)ethanol (14)

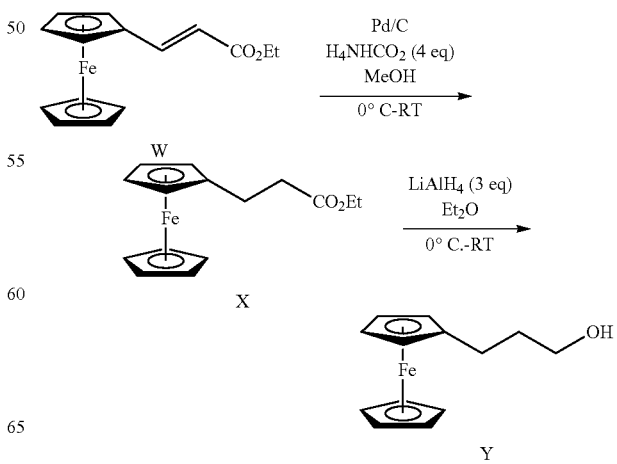

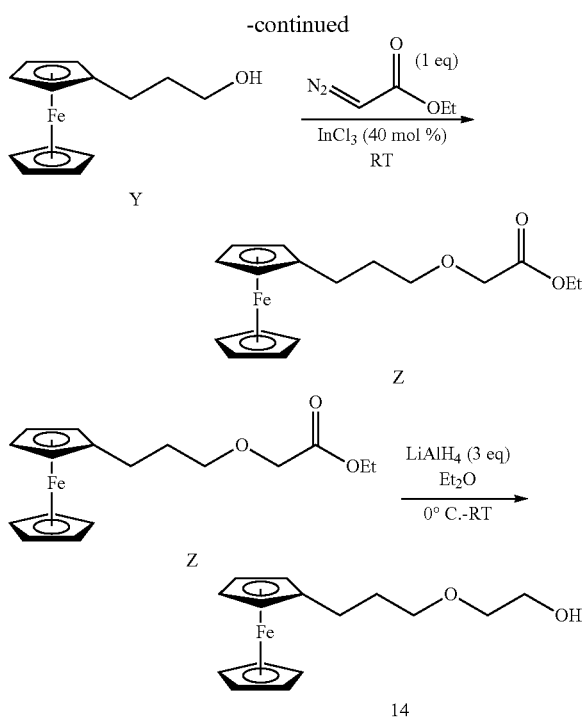

Ethyl-3-ferrocenyl acrylate (W) was prepared according to the procedure in Tetrahedron, 2009, 65, 672-676.

Ethyl-3-ferrocenyl Propanoate (X)

The ethyl-3-ferrocenyl acrylate (W) (7.43 g, 23.3 mmol, 1 eq) was dissolved in MeOH (125 cm$^3$) and cooled to 0° C. Once cold the palladium on carbon (10% wt) (1.5 g) and ammonium formate (5.87 g, 93.2 mmol, 4 eq) were added sequentially. The black suspension was allowed to warm to room temperature and then stirred for 1 hour. The suspension was filtered through celite, and the solids washed with MeOH (100 cm$^3$). The orange solution was then concentrated in vacuo to give an orange solid, which was then taken up in EtOAc (100 cm$^3$) and NaHCO$_3$ (50 cm$^3$). The organic layer was separated and the aqueous layer back extracted with EtOAc (3×50 cm$^3$). The combined organics were then dried over MgSO$_4$, filtered and concentrated in vacuo to give the desired product ethyl-3-ferrocenyl propanoate (X) as an orange oil (4.86 g, 73%) without the need for further purification.

$^1$H NMR (250 MHz, CDCl$_3$); $\delta_H$: 4.2 (d, J=7.0, 2H), 4.09 (s, 2H), 4.02 (s, 7H), 2.93-2.87 (m, 2H), 2.54-2.49 (m, 2H), 2.52 (1H, br s), 1.37 (t, J=7.0 Hz, 3H); $^{13}$C NMR (75 MHz, CDCl$_3$); $\delta_C$: 170.5, 77.5, 77.0, 76.6, 69.8, 61.3, 34.8, 23.2, 15.3.

Ferrocene Propanol (Y)

To a suspension of lithium aluminium hydride (1.94 g, 51 mmol, 3 eq) in dry Et$_2$O (120 cm$^3$) at 0° C. was added ethyl-3-ferrocenyl propanoate (X) (4.86 g, 17 mmol, 1 eq) in dry Et$_2$O (30 cm$^3$) dropwise over a 25 minute period. Once the addition was complete the suspension was allowed to warm to room temperature and stirred for 1 hour. After this time the flask was cooled to 0° C. and the reaction was quenched by sequential dropwise addition of H$_2$O (1.9 cm$^3$), 15% NaOH (aq) (1.9 cm$^3$) and H$_2$O (5.7 cm$^3$). The yellow suspension was then allowed to warm to room temperature and was stirred for 10 minutes. The suspension was filtered, and solids washed with Et$_2$O (75 cm$^3$) until the washing ran clear. The orange solution was dried over MgSO$_4$, filtered and concentrated in vacuo to give ferrocene propanol (Y) as an orange oil (4.19 g, 99%) without the need for further purification.

$^1$H NMR (300 MHz, CDCl$_3$); $\delta_H$: 4.19 (s, 9H), 3.65 (t, J=6.0 Hz, 2H), 2.55 (d, J=6.0 Hz, 2H), 1.70 (t, J=6.0 Hz, 2H); $^{13}$C NMR (75 MHz, CDCl$_3$); $\delta_C$: 77.8, 77.6, 77.4, 76.9, 63.4, 38.5, 29.4.

Ethyl 2-ferrocenethoxyacetate (Z)

The ferrocene propanol (Y) (1.93 g, 7.9 mmol, 1 eq) was placed in a round bottomed flask and treated with ethyl diazoacetate (552 µl, 5.26 mmol, 0.66 eq) and indium (III) chloride (464 mg, 2.1 mmol, 40 mol %). The slurry was allowed to stir at room temperature under nitrogen for 16 hours. After this time the slurry was diluted with EtOAc (25 cm$^3$) and H$_2$O (25 cm$^3$). The organic layer was separated and the aqueous layer back extracted with EtOAc (3×20 cm$^3$). The combined organics were washed with brine (sat) (50 cm$^3$), dried over MgSO$_4$, filtered and concentrated in vacuo to give an orange oil. Purification by silica chromatography eluting with 15% EtOAc:n-Hex gave the desired product ethyl 2-ferrocenethoxyacetate (Z) as an orange oil (993 mg, 57%).

$^1$H NMR (300 MHz, C$_6$D$_6$) $\delta_H$ 4.11-4.06 (m, 8H), 4.04-3.98 (m, 5H), 3.94 (s, 2H), 2.50 (dd, J=8.7, 6.8 Hz, 2H), 1.94-1.80 (m, 2H), 1.00 (t, J=7.1 Hz, 3H); $^{13}$C NMR (75 MHz, C$_6$D$_6$) $\delta_H$ 170.5, 89.2, 71.6, 69.2, 68.9, 68.3, 67.9, 60.6, 32.0, 26.6, 14.5.

2-(3-Ferrocenylpropoxy)ethanol (14)

To a suspension of lithium aluminium hydride (343 mg, 9 mmol, 3 eq) in dry Et$_2$O (10 cm$^3$) at 0° C. was added the ethyl 2-ferrocenethoxyacetate (Z) (993 mg, 3 mmol, 1 eq). in dry Et$_2$O (5 cm$^3$) dropwise over a 5 minute period. The suspension was allowed to warm to room temperature and stirred for 30 minutes. After this time the flask was cooled to 0° C. and the reaction was quenched by sequential dropwise addition of H$_2$O (343 µl), 15% NaOH (aq) (343 µl) and H$_2$O (1.2 cm$^3$). The yellow suspension was then allowed to warm to room temperature and was stirred for 10 minutes. The suspension was filtered, and solids washed with Et$_2$O (25 cm$^3$) until the washings ran clear. The orange solution was dried over MgSO$_4$, filtered and concentrated in vacuo to give an orange oil. Purification by silica chromatography eluting with 20% EtOAc:n-Hex gave the desired product 2-(3-ferrocenylpropoxy)ethanol as an orange oil (739 mg, 85%).

$^1$H NMR (300 MHz, C$_6$D$_6$) $\delta_H$ 3.90 (s, 5H), 3.85 (s, 4H), 3.47-3.35 (m, 2H), 3.11 (dd, J=10.4, 5.4 Hz, 4H), 2.29-2.14 (m, 2H), 1.67-1.47 (m, 3H); $^{13}$C NMR (75 MHz, C$_6$D$_6$) $\delta_C$ 89.1, 72.6, 71.1, 69.2, 68.8, 67.9, 62.3, 31.9, 26.8; HRMS (ESI µTOF) calculated for C$_{15}$H$_{21}$FeO$_2$ m/z 289.1553 found 289.0987 (m/z+H); Electrochemical potential: 114 mV.

Example 15: Preparation of 2-(3-(2-tert-butylthio)-ferrocenylpropoxy)ethanol (15)

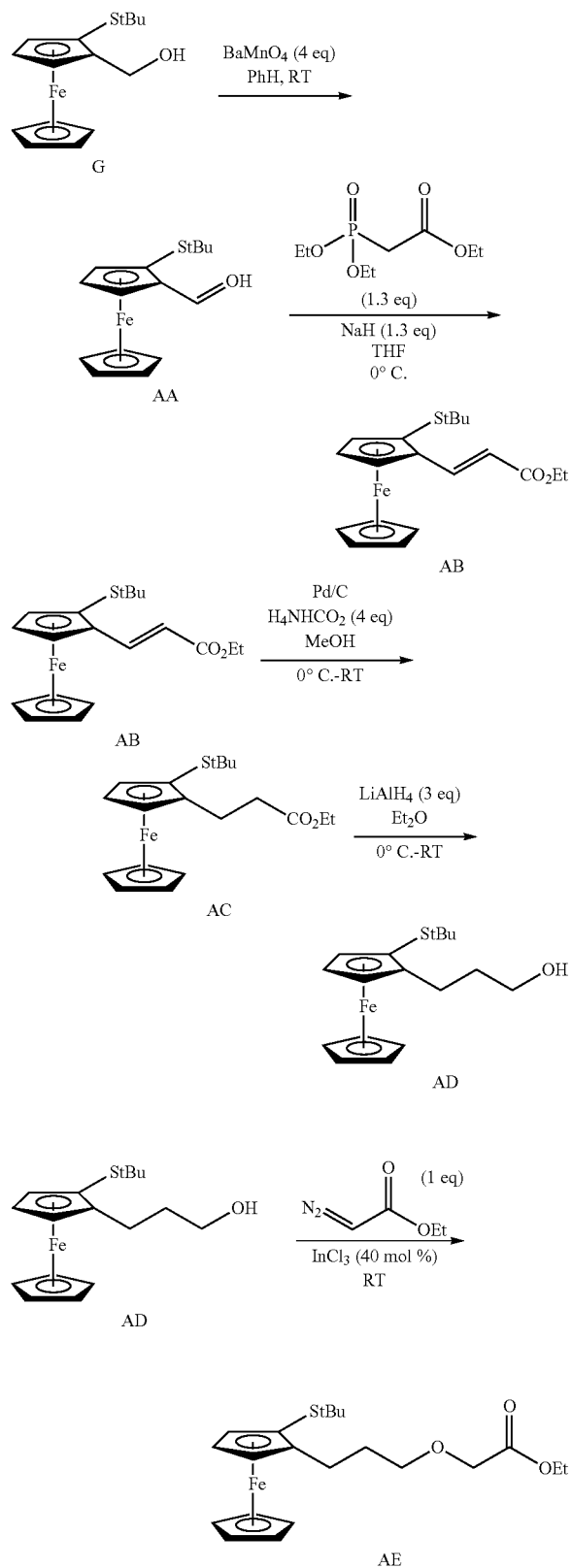

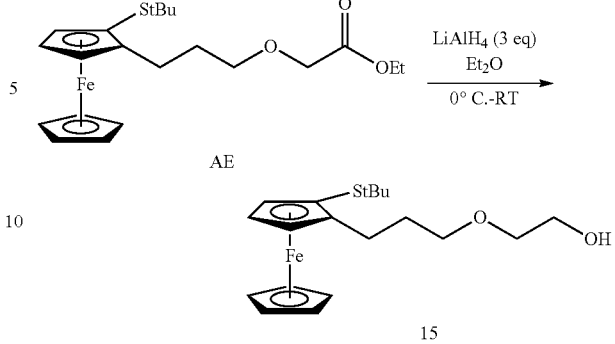

2-tert-butylthio-ferrocene Carboxaldehyde (AA)

The 2-tert-butylthio ferrocene methanol (G) (741 mg, 2.4 mmol, 1 eq) was placed in a Schlenk tube with barium manganate (2.49 g, 9.7 mmol, 4 eq). The flask was sealed, then evacuated and backfilled under argon four times. The flask was then charged with benzene (15 cm$^3$). The resulting dark blue slurry was then stirred at room temperature for 16 hours. After this time the slurry was filtered through celite and solids washed with Et$_2$O (25 cm$^3$) until washings ran clear. The resulting red solution was concentrated in vacuo to give the desired aldehyde 2-tert-butylthio-ferrocene carboxaldehyde (AA) as a red oil (668 mg, 92%) without the need for further purification.

$^1$H NMR (300 MHz, C$_6$D$_6$) $\delta_H$ 10.66 (s, 1H), 5.09-5.01 (m, 1H), 4.45 (dd, J=2.4, 1.7 Hz, 1H), 4.19 (dd, J=2.4, 1.7 Hz, 1H), 4.04 (s, 5H), 1.14 (s, 9H); $^{13}$C NMR (75 MHz, C$_6$D$_6$) $\delta_C$ 193.4, 82.3, 81.7, 81.1, 73.2, 71.5, 69.6, 45.9, 30.9; HRMS (ESI μTOF) calculated for C$_{15}$H$_{18}$FeOSNa m/z 325.0325 found 325.0325 (m/z+Na$^+$).

Ethyl-3-(2-tert-butylthio-ferrocenyl) Acrylate (AB)

To a suspension of sodium hydride (60% dispersion in oil) (109 mg, 2.85 mmol, 1.3 eq) in dry THF (10 cm$^3$) at 0° C. was added triethylphosphonacetate (571 ml, 2.85 mmol, 1.3 eq) dropwise over a 5 minute period. Once addition was complete the solution was allowed to warm to room temperature and stirred for 30 mins. After this time the solution was cooled to 0° C. Once cold the 2-tert-butyl-ferrocene carboxaldehyde (AA) (668 mg, 2.2 mmol, 1 eq) in dry THF (5 cm$^3$) was added dropwise over a 5 min period. Once addition was complete the flask was allowed to warm to room temperature and was stirred for an additional 30 minutes. After this time the reaction was quenched by addition of H$_2$O (20 cm$^3$). The organic layer was then separated and the aqueous layer back extracted with EtOAc (3×5 cm$^3$). The combined organics were then washed with brine (sat) (10 cm$^3$), dried over MgSO$_4$, filtered and concentrated in vacuo to give a red oil. Purification by silica chromatography eluting with 5% EtOAc:n-Hex gave the desired product ethyl-3-(2-tert-butylthio-ferrocenyl) acrylate (AB) as a red oil (823 mg, 99%).

$^1$H NMR (300 MHz, C$_6$D$_6$) $\delta_H$ 8.50 (d, J=16.0 Hz, 1H), 6.48 (d, J=16.0 Hz, 1H), 4.50 (dd, J=2.5, 1.4 Hz, 1H), 4.44 (dd, J=2.5, 1.4 Hz, 1H), 4.23 (qd, J=7.1, 2.2 Hz, 2H), 4.16 (t, J=2.5 Hz, 1H), 4.01 (s, 4H), 1.21 (s, 9H), 1.14 (t, J=7.1 Hz, 3H); $^{13}$C NMR (75 MHz, C$_6$D$_6$) $\delta_H$ 185.5, 167.2, 144.8, 116.4, 83.4, 79.9, 72.6, 71.7, 71.4, 67.3, 60.5, 51.1, 46.2, 40.4, 31.1, 20.3, 14.8, 10.0; HRMS (ESI μTOF) calculated for $C_{19}H_{24}FeO_2SNa$ m/z 395.0744 found 395.0748 (m/z+$Na^+$).

Ethyl-3-(2-tert-butylthioferrocenyl) Propanoate (AC)

The ethyl-3-(2-tert-butylthio-ferrocenyl) acrylate (AB) (823 mg, 2.2 mmol, 1 eq) was dissolved in methanol (15 cm$^3$) and cooled to 0° C. Once cold, palladium on carbon (10% wt) (1 g) and ammonium formate (831 mg, 13.2 mmol, 6 eq) were added. The suspension was allowed to warm to room temperature and stirred for 4 hours. After this time suspension was filtered through celite and the solids were washed with methanol (25 cm$^3$) until washings ran clear. The orange solution was then concentrated in vacuo to give an orange solid. This was partitioned between EtOAc (25 cm$^3$) and NaHCO$_3$ (sat) (25 cm$^3$). The organic layer was separated and the aqueous layer back extracted with EtOAc (3×5 cm$^3$). The combined organics were dried over MgSO$_4$, filtered and concentrated in vacuo to give the desired material Ethyl-3-(2-tert-butylthioferrocenyl) propanoate (AC) as an orange oil (617 mg, 75%) without the need for further purification.

$^1$H NMR (300 MHz, C$_6$D$_6$) δ$_H$ 4.42 (dd, J=2.3, 1.4 Hz, 1H), 4.14-4.10 (m, 3H), 4.08 (s, 5H), 4.04 (t, J=2.5 Hz, 1H), 3.17 (ddd, J=15.4, 8.9, 6.7 Hz, 1H), 3.00 (ddd, J=15.4, 8.9, 6.7 Hz, 1H), 2.79-2.60 (m, 2H), 1.26 (s, 9H), 1.09 (t, J=7.1 Hz, 3H); $^{13}$C NMR (75 MHz, C$_6$D$_6$) δ$_C$ 173.1, 92.3, 77.3, 76.9, 70.7, 69.0, 68.4, 60.6, 45.9, 35.6, 31.4, 23.8, 14.7; HRMS (ESI μTOF) calculated for $C_{19}H_{26}FeO_2SNa$ m/z 397.0900 found 397.0917 (m/z+$Na^+$).

2-tert-butylthioferrocene Propanol (AD)

To a suspension of lithium aluminium hydride (188 mg, 4.9 mmol, 3 eq) in dry Et$_2$O (3.5 cm$^3$) at 0° C. was added ethyl-3-(2-tert-butylthioferrocenyl) propanoate (AC) (617 mg, 16 mmol, 1 eq) in dry Et$_2$O (4 cm$^3$) was added dropwise over a 2 minute period. Once the addition was complete the suspension was allowed to warm to room temperature and stirred for 30 mins. After this time the flask was cooled to 0° C. and the reaction was quenched by sequential dropwise addition of H$_2$O (188 μl), 15% NaOH (aq) (188 μl) and H$_2$O (546 μl). The yellow suspension was then allowed to warm to room temperature and was stirred for 10 minutes. The suspension was filtered, and solids washed with Et$_2$O (15 cm$^3$) until the washing ran clear. The orange solution was dried over MgSO$_4$, filtered and concentrated in vacuo to give 2-tert-butylthioferrocene propanol (AD) as an orange oil (381 mg, 66%) without the need for further purification.

$^1$H NMR (300 MHz, C$_6$D$_6$) δ$_H$ 4.45 (dd, J=2.4, 1.4 Hz, 1H), 4.17-4.15 (m, 1H), 4.14 (s, 5H), 4.09 (t, J=2.5 Hz, 1H), 3.56 (t, J=6.4 Hz, 2H), 2.79 (ddd, J=14.9, 11.2, 5.6 Hz, 1H), 2.58 (ddd, J=14.9, 11.2, 5.6 Hz, 1H), 1.97-1.71 (m, 2H), 1.30 (s, 9H); $^{13}$C NMR (75 MHz, C$_6$D$_6$) δ$_C$ 93.5, 77.2, 76.7, 70.7, 69.1, 68.3, 63.2, 45.8, 34.0, 31.8, 24.8; HRMS (ESI μTOF) calculated for $C_{17}H_{24}FeOSNa$ m/z 355.0794 found 355.0780 (m/z+$Na^+$).

Ethyl 2-(2-tert-butylthioferrocene)ethoxyacetate (AE)

The 2-tert-butylthioferrocene propanol (AD) (483 mg, 1.29 mmol, 1 eq) was placed in a round bottomed flask and treated with ethyl diazoacetate (552 μl, 5.26 mmol, 4 eq) and indium (III) chloride (114 mg, 0.52 mmol, 40 mol %). The slurry was allowed to stir at room temperature under nitrogen for 16 hours. After this time the slurry was diluted with EtOAc (25 cm$^3$) and H$_2$O (15 cm$^3$).

The organic layer was separated and the aqueous layer back extracted with EtOAc (3×5 cm$^3$). The combined organics were washed with brine (sat) (10 cm$^3$), dried over MgSO$_4$, filtered and concentrated in vacuo to give an orange oil. Purification by silica chromatography eluting with 10% EtOAc:n-Hex gave the desired product as an orange oil (164 mg, 30%).

$^1$H NMR (300 MHz, C$_6$D$_6$) δ$_H$ 4.45 (dd, J=2.5, 1.4 Hz, 1H), 4.19 (dd, J=2.5, 1.4 Hz, 1H), 4.14 (s, 5H), 4.09-3.97 (m, 9H), 3.59 (td, J=8.6, 2.3 Hz, 2H), 2.90 (ddd, J=15.0, 11.1, 5.6 Hz 1H), 2.69 (ddd, J=15.0, 11.1, 5.6 Hz 1H), 2.18-1.91 (m, 2H), 1.30 (s, 9H), 1.02 (t, J=6.3 Hz, 3H); $^{13}$C NMR (75 MHz, C$_6$D$_6$) δ$_C$ 170.6, 93.5, 77.2, 76.7, 72.2, 70.7, 69.2, 68.9, 68.3, 61.0, 60.7, 45.8, 31.5, 31.2, 25.0, 14.7, 14.6; HRMS (ESI TOF) calculated for $C_{21}H_{30}FeO_3SNa$ m/z 441.1162 found 441.1179 (m/z+$Na^+$).

2-(3-(2-tert-butylthio)-ferrocenylpropoxy)ethanol (15)

To a suspension of lithium aluminium hydride (44 mg, 1.17 mmol, 3 eq) in dry Et$_2$O (2 cm$^3$) at 0° C. was added the ethyl 2-(2-tert-butylthioferrocene)ethoxyacetate (AE) (164 mg, 0.39 mmol, 1 eq). in dry Et$_2$O (1 cm$^3$) dropwise over a 2 minute period. The suspension was allowed to warm to room temperature and stirred for 30 minutes. After this time the flask was cooled to 0° C. and the reaction was quenched by sequential dropwise addition of H$_2$O (44 μl), 15% NaOH (aq) (44 μl) and H$_2$O (132 cm$^3$). The yellow suspension was then allowed to warm to room temperature and was stirred for 10 minutes. The suspension was filtered, and solids washed with Et$_2$O (10 cm$^3$) until the washings ran clear. The orange solution was dried over MgSO$_4$, filtered and concentrated in vacuo to give an orange oil. Purification by silica chromatography eluting with 20% EtOAc:n-Hex gave the desired product 2-(3-(2-tert-butylthio)-ferrocenylpropoxy)ethanol (15) as an orange oil (41 mg, 28%).

$^1$H NMR (300 MHz, C$_6$D$_6$) δ$_H$ 4.46 (dd, J=2.6, 1.4 Hz, 1H), 4.19 (dd, J=2.6, 1.4 Hz, 1H), 4.15 (s, 5H), 4.10 (t, J=2.6 Hz, 1H), 3.67 (dd, J=9.7, 5.3 Hz, 2H), 3.43 (t, J=6.5 Hz, 2H), 3.37 (t, J=6.5 Hz 2H), 2.81 (ddd, J=14.9, 11.1, 5.7 Hz, 1H), 2.63 (ddd, J=14.9, 11.1, 5.7 Hz, 1H), 2.13 (t, J=5.9 Hz, 1H), 2.09-1.85 (m, 2H), 1.30 (s, 9H); $^{13}$C NMR (75 MHz, C$_6$D$_6$) δ$_C$ 93.4, 77.2, 76.8, 72.8, 71.8, 70.7, 69.1, 68.3, 62.3, 45.8, 31.5, 31.2, 25.1; HRMS (ESI TOF) calculated for $C_{19}H_{28}FeO_2SNa$ m/z 399.1057 found 399.1063 (m/z+$Na^+$); Electrochemical potential: 297 mV.

Example 16: Preparation of 2-(3-(2-tert-butylsulfinyl)-ferrocenylpropoxy)ethanol (16)

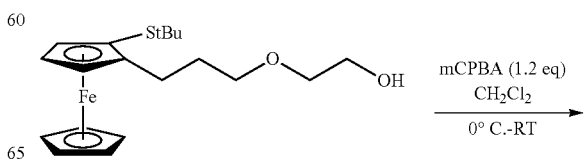

15

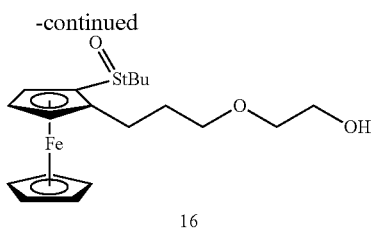

16

The 2-(3-(2-tert-butylthio)-ferrocenylpropoxy)ethanol (15) (40 mg, 0.11 mmol, 1 eq) was dissolved in $CH_2Cl_2$ (2 $cm^3$), the flask was then placed under a nitrogen atmosphere and cooled to 0° C. Once cold 3-chloro-perbenzoic acid (22 mg, 0.127 mmol, 1.2 eq) was added in one portion. The solution was then stirred at 0° C. for 15 minutes. After this time TLC analysis indicated full consumption of the starting material. The reaction was then quenched by addition of $NaHCO_3$ (sat) (5 $cm^3$) and stirred vigorously for 5 minutes. After this time the organic layer was separated and aqueous layer extracted with $CH_2Cl_2$ (3×5 $cm^3$). The combined organic were then washed with brine (sat) (10 $cm^3$), dried over $MgSO_4$, filtered and concentrated in vacuo to give a dark brown oil. Purification by silica chromatography eluting with EtOAc gave the desired product 2-(3-(2-tert-butylsulfinyl)-ferrocenylpropoxy)ethanol (16) as a yellow solid (12 mg, 29%).

$^1$H NMR (300 MHz, $C_6D_6$) $\delta_H$ 4.81 (s, 1H), 4.41 (s, 5H), 4.10 (t, J=2.4 Hz, 1H), 4.07 (s, 1H), 3.75 (t, J=6.2 Hz, 2H), 3.46 (t, J=6.2 Hz, 2H), 3.40 (t, J=6.2 Hz, 2H), 2.68 (ddd, J=15.2, 11.5, 4.7 Hz 1H), 2.34 (ddd, J=15.2, 11.5, 4.7 Hz 1H), 2.0-1.91 (m, 1H), 1.90-1.78 (m, 1H), 1.13 (s, 9H); $^{13}$C NMR (75 MHz, $C_6D_6$) $\delta_C$ 92.1, 88.0, 73.0, 71.4, 69.6, 68.6, 65.9, 62.3, 56.1, 30.6, 25.5, 23.4; HRMS (ESI µTOF) calculated for $C_{19}H_{28}FeO_3SNa$ m/z 415.1006 found 415.1010 (m/z+$Na^+$); Electrochemical potential: 397 mV.

Example 17: Preparation of 2-(3-(2-tert-butylsulfonyl)-ferrocenylpropoxy)ethanol (17)

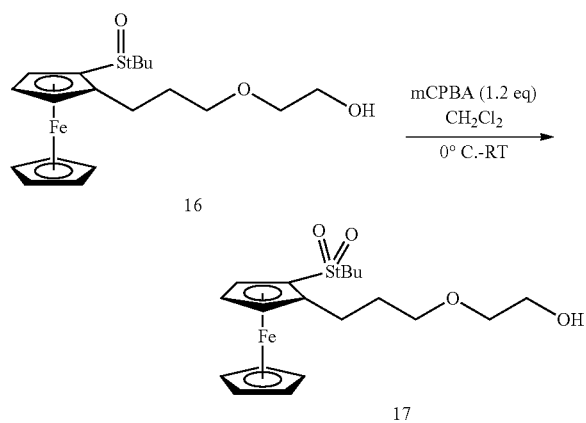

2-(3-(2-tert-butylsulfinyl)-ferrocenylpropoxy)ethanol (16) (12 mg, 0.03 mmol, 1 eq) was dissolved in $CH_2Cl_2$ (1 $cm^3$), placed under a nitrogen atmosphere and cooled to 0° C. Once cold, 3-chloro-perbenzoic acid (6.3 mg, 0.036 mmol, 1.2 eq) was added in one portion. The solution was then stirred at 0° C. for 15 minutes. After this time TLC analysis indicated full consumption of the starting material. The reaction was then quenched by addition of $NaHCO_3$ (sat) (5 $cm^3$) and stirred vigorously for 5 minutes. After this time the organic layer was separated and aqueous layer extracted with $CH_2Cl_2$ (3×5 $cm^3$). The combined organics were then washed with brine (sat) (10 $cm^3$), dried over $MgSO_4$, filtered and concentrated in vacuo to give a dark brown oil. Purification by silica chromatography eluting with EtOAc gave the desired product 2-(3-(2-tert-butylsulfonyl)-ferrocenylpropoxy)ethanol (17) as a yellow oil (4 mg, 33%).

$^1$H NMR (300 MHz, $C_6D_6$) $\delta_H$ 4.58 (dd, J=2.4, 1.6 Hz, 1H), 4.41 (s, 4H), 4.09 (dd, J=2.4, 1.6 Hz, 1H), 4.01 (t, J=2.4 Hz, 1H), 3.65 (t, J=4.5 Hz, 2H), 3.4-3.34 (m, 4H), 3.15 (ddd, J=15.3, 11.9, 5.2 1H), 2.65 (ddd, J=15.3, 11.9, 5.2, Hz 1H), 2.0-1.73 (m, 4H), 1.23 (s, 9H); $^{13}$C NMR (75 MHz, $C_6D_6$) $\delta_H$ 101.9, 91.8, 88.7, 82.9, 75.7, 72.8, 72.7, 72.0, 71.5, 71.0, 69.3, 62, 59.4, 36.2, 30.9, 24.7, 24.1, 24.0; HRMS (ESI TOF) calculated for $C_{19}H_{28}FeO_4SNa$ m/z 431.0955 found 431.0954 (m/z+$Na^+$); Electrochemical potential: 489 mV.

Example 18: Preparation of 2-cyanoethyl-(2-(3-ferrocenylpropoxy)ethanol)diisopropyl-phosphoramidite

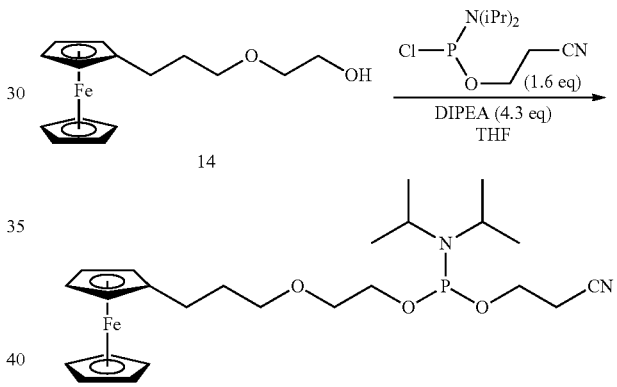

To an oven dried 100 $cm^3$ round bottomed flask equipped with a magnetic stirrer was added the 2-(3-ferrocenylpropoxy)ethanol (14) (753 mg, 2.6 mmol, 1 eq). The flask was then sealed and purged with $N_2$. The yellow powder was then dissolved in dry THF (25 $cm^3$) to give an orange solution, this was then immediately treated with DIPEA (1.95 ml, 11.2 mmol, 4.3 eq). The 2-cyanoethyl-N,N-diisopropylchlorophosphoramidite (1 g, 4.2 mmol, 1.6 eq) was then added to the 14 solution over a 2 min period. Once complete the orange solution was allowed to stir for 10 mins. $H_2O$ (200 µl) was then added and the orange solution stirred for a further 30 mins under nitrogen. The reaction was then quenched by addition of EtOAc:TEA (1:1, 25 $cm^3$). The mixture was then washed with $NaHCO_3$ (sat) (10 $cm^3$) and brine (sat) (10 $cm^3$). The orange organic layer was then dried over $Na_2SO_4$, filtered, then concentrated in vacuo to give a yellow oil. Purification by silica chromatography (ø5×10 $cm^3$, $CH_2Cl_2$ wet load) eluting with 10% EtOAc:n-Hex+1% triethylamine under a nitrogen exit stream gave the desired product 2-cyanoethyl-(2-(3-ferrocenylpropoxy)ethanol)diisopropylphosphoramidite as an orange oil (946 mg, 78%).

$^1$H NMR (300 MHz, $CDCl_3$) $\delta_H$ 4.09 (s, 5H), 4.06-4.04 (m, 4H), 3.88-3.79 (m, 2H), 3.60 (t, J=5.4 Hz, 2H), 3.48 (t, J=6.5 Hz, 2H), 2.65 (t, J=6.6 Hz, 2H), 2.44-2.32 (m, 2H), 1.79 (dt, J=14.1, 6.5 Hz, 2H), 1.19 (d, J=6.8 Hz, 12H); $^{13}$C NMR (75 MHz, CDCl$_3$) δ$_C$ 117.7, 88.7, 70.9, 70.8, 70.7, 68.4, 68.0, 67.1, 62.8, 62.5, 58.6, 58.3, 43.1, 42.9, 31.0, 26.0, 24.7, 24.6, 24.6, 24.5, 20.4, 20.3; $^{31}$P{$^1$H} NMR (122 MHz, CDCl$_3$) δp 149.18. HRMS (ESI μTOF) calculated for C$_{24}$H$_{37}$FeN$_2$O$_3$PNa m/z 511.1886 found 511.1893 (m/z+ Na$^+$).

Example 19: 2-cyanoethyl-(3-(Nonamethylferrocenylmethoxy)propan-1-ol)di-iso-propyl-phosphoramidite

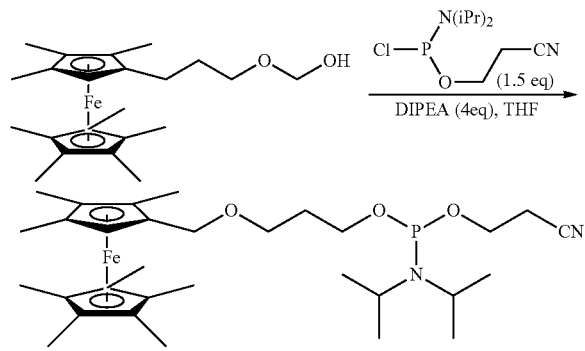

To an oven dried 100 cm$^3$ round bottomed flask equipped with a magnetic stirrer was added the 3-(nonamethylferrocenylmethoxy)propan-1-ol (2) (1.12 g, 2.8 mmol, 1 eq). The flask was then sealed and purged with N$_2$. The yellow powder was then dissolved in dry THF (25 cm$^3$) to give an orange solution, this was then immediately treated with DIPEA (1.95 ml, 11.2 mmol, 4 eq). The 2-cyanoethyl-N,N-diisopropylchlorophosphoramidite (1 g, 4.2 mmol, 1.5 eq) was then added to the 2 solution over a 2 min period. Once complete the orange solution was allowed to stir for 10 mins. H$_2$O (200 μl) was then added and the orange solution stirred for a further 30 mins under nitrogen. The reaction was then quenched by addition of EtOAc:TEA (1:1, 25 cm$^3$). The mixture was then washed with NaHCO$_3$ (sat) (10 cm$^3$) and brine (sat) (10 cm$^3$). The orange organic layer was then dried over Na$_2$SO$_4$, filtered, then concentrated in vacuo to give a yellow oil. Purification by silica chromatography (05×10 cm$^3$, CH$_2$Cl$_2$ wet load) eluting with 10% EtOAc:n-Hex+1% triethylamine under a nitrogen exit stream gave the desired product as an orange oil (995 mg, 59%).

$^1$H NMR (300 MHz, C$_6$D$_6$) δ$_H$ 4.43 (d, 1H, J=11.3), 4.38 (d, 1H, J=11.3) 3.99-3.75 (m, 2H), 3.72-3.56 (m, 4H), 3.52-3.33 (m, 2H), 2.0-1.77 (m, 10H), 1.73 (s, 21H), 1.23 (t, J=6.4, 6H); $^{31}$P {$^1$H}NMR (122 MHz, C$_6$D$_6$) δ$_P$ 148.75 (s); $^{13}$C NMR (75 MHz, C$_6$D$_6$) δ$_C$ 90.4, 80.4, 80.2, 79.2, 78.0, 71.9, 66.7, 66.5, 63.9, 61.3, 59.1, 47.2, 43.7, 43.6, 37.3, 32.7, 30.8, 25.1, 25.0, 25.0, 20.4, 16.6, 10.2, 10.1, 9.93; HRMS (ESI μTOF) calculated for C$_{32}$H$_{53}$FeNO$_3$PNa m/z 623.3041 found 623.3031 (m/z+Na$^+$).

The electrochemical data show that compounds of the invention provide useful electrochemically active labels. The labels may be used to provide an electrochemical signal within a desired range of values. They may be useful as alternative labels to other labelling compounds with similar potential values, for example, where those other labelling compounds have disadvantageous properties in the assay in question, for example, incompatibility with impurities or other components present in the assay or incompatibility with the measurement conditions, any of which could affect measurement sensitivity. As well, or instead, they may be used with one or more other labels in a multiplex assay in which more than one label is present to provide two or more determinations in a single sample, the use of two or more labels with different electrochemical properties in those circumstances permitting effective distinction between measurements relating to the respective species to be determined (e.g. see Example 22). The compounds of the invention also give consistent electrochemical responses making them useful as internal controls in assays.

Example 20—Binding of Labels to Protein

Labels of the invention are attached to a peptide via a free amine of, for example, a lysine residue in the peptide. Attachment may be accomplished conventional techniques including functionalisation of the labelling compound to form an active NHS (N-hydroxysuccinimide) ester and reaction of the functionalised ester with the free amine group of the peptide.

Example 21—Binding of Labels to Particles

A biotin molecule is coupled to a label, for example a label as made in any of the above examples. The biotinylation can be carried out in an automated oligonucleotide synthesiser or using standard laboratory conditions by reaction of a ferrocenyl phosphoramidite label with NHS esters of biotin.

Paramagnetic streptavidin particles are washed ×3 (phosphate buffer) and mixed with biotinylated label, followed by incubation for 1 hour at room temperature with mixing. The particles are washed ×2 (phosphate buffer) and washed ×1 (PCR buffer). They are resuspended in final buffer (PCR buffer). Following each wash step the supernatants are tested for electrochemical signal, and if necessary washing is repeated until the supernatants show no indication of free electrochemical label.

These particles are assayed at a range of concentrations to validate that the observed electrochemical signal is attributable to the label coupled to the magnetic particles, using magnetic capture of the particles and resuspension in a range of buffer volumes.

Example 22—Multiplex PCR Assay

The ferrocene compounds 2, 14, and 6 were converted in their corresponding phosphoramidites using the procedures described herein. Two diferrocene labels were also converted to phosphoramidites, namely 6-(bis-methylferrocenyl)amino)hexan-1-ol ('di-1') and 6-(bis((1'-chloroferrocenyl) 1-methylferrocenyl)amino)hexan-1-ol ('di-2'). Using standard solid phase coupling methodologies these five phosphoramidites were then coupled at the 5'-end to five oligonucleotide probes, each designed to detect a specific gene. The labels and probe targets were as follows:

| Label | Target | Label | Target |
|---|---|---|---|
| 2 | Internal control | di-1 | C. trachomatis gene |
| 14 | S. aureus gene | di-2 | N. gonorrhoeae gene |
| 6 | T. vaginalis gene | | |

PCR was performed on various samples using primers designed for the five target genes listed in this table. The separate amplifications were them combined to give a 5-plex mixture, and the five labelled probes were then added to this mixture, together with T7 exonuclease. This mixture was incubated and detection was performed essentially as set out in Pearce et al. using screen-printed electrodes.

FIG. 1 shows six superimposed voltammograms: three performed on samples containing the various target genes (positive control), and three performed on blank samples (negative control):

The three negative control samples show no visible peaks between −0.5 and +0.7 volts. In contrast, the three positive control samples each show five separate peaks. From left to right, these peaks correspond to labels 2, 14, di-1, di-2, and 6. Thus the monoferrocene labels of the invention are useful as labels in nucleic acid hybridisation assays, including multiplex assays, and they can be used also in combination with diferrocene labels.

Figure 2:
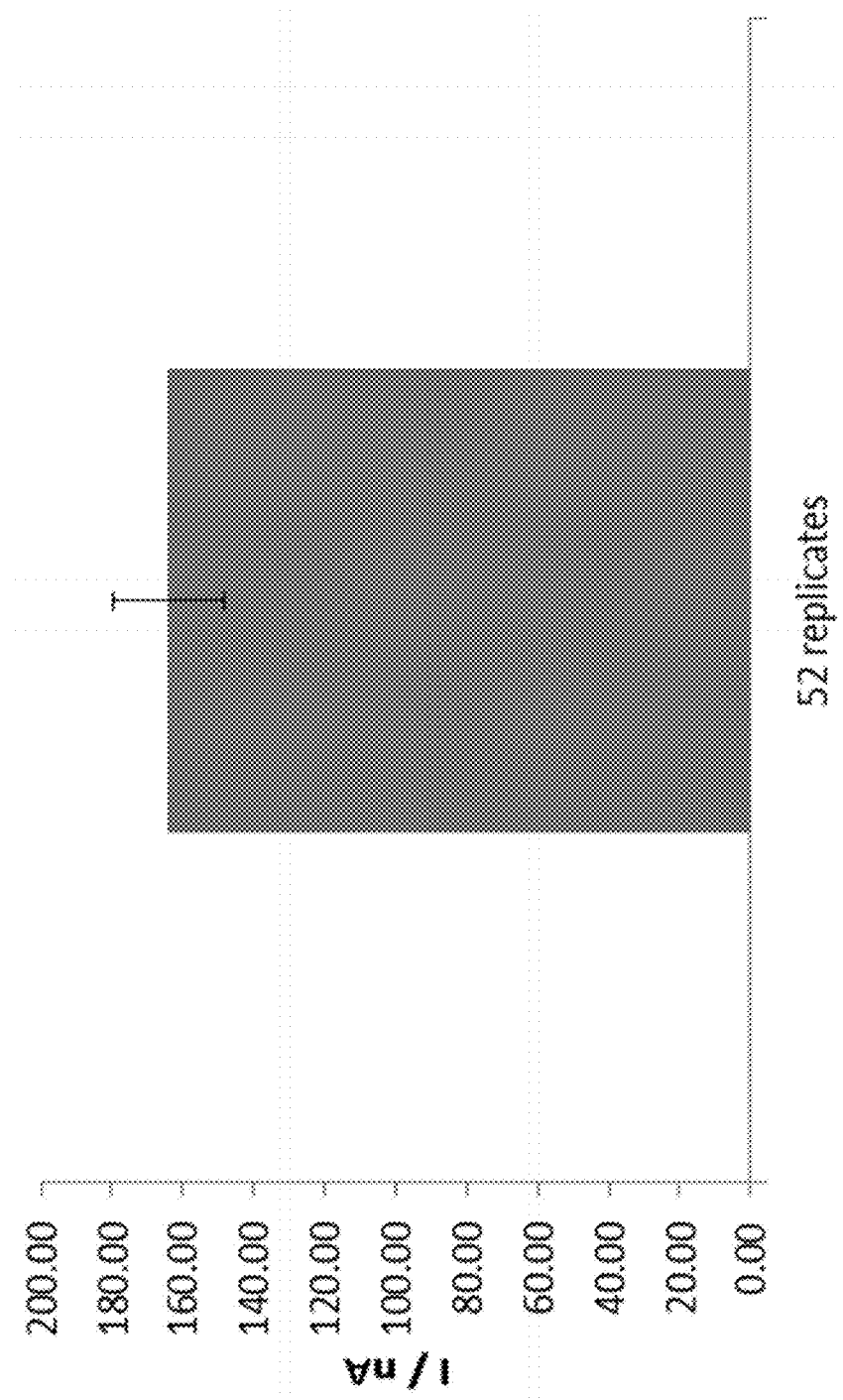
FIG. 2 shows a graph cataloguing the use of 3-(nonamethylferrocenylmethoxy)propan-1-ol (example compound 2) as a probe in a series of detection assays, as described in example 23.

Example 23—Reproducibility Experiment 3-(nonamethylferrocenylmethoxy)propan-1-ol (example compound 2) was conjugated to an oligonucleotide using standard conditions. The resulting probe was utilised at concentration of 5 µM in 52 separate PCRs amplifying 1000 copies of DNA. Electrochemical detection of the probe yielded the current data in FIG. 2.

This data shows that the compounds of the invention give consistent, reproducible electrochemical signals. This makes the compounds of the invention particularly useful in assays, for example as internal controls.

It will be understood that the invention is described above by way of example only and modifications may be made whilst remaining within the scope and spirit of the invention.

The invention claimed is:
1. A compound of formula IA'

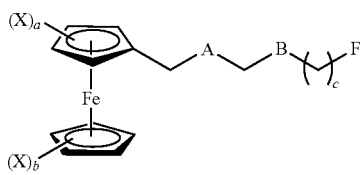

wherein:
each X substituent is independently selected from the group consisting of halo, vinyl, alkyl, cycloalkyl, $SiR_3$, $SnR_3$, $PR_2$, $P(O)R_2$, SR, S(O)R, $SO_2R$, aryl, heteroaryl, CHO, $CO_2R$, CN and $CF_3$;
each R is independently selected from the group consisting of alkyl, aryl, cycloalkyl, and heteroaryl;
A is $CH_2$, B is O and c is 2;
a is 0, 1, 2, 3 or 4 and b is 0; and
vinyl, alkyl, cycloalkyl, aryl and heteroaryl may optionally be substituted with 1, 2 or 3 substituents independently selected from the group consisting of unsubstituted OH, CN, fluorine, chlorine, bromine, and iodine,
wherein F comprises a group selected from the group consisting of succinimidyl ester groups, phosphoramidite groups, maleimide groups, biotin groups, and azide groups; and
wherein said compound has an electrochemical potential of at least 450 mV.

2. The compound of claim 1 selected from the group consisting of:
2-cyanoethyl-(3-(ferrocenylmethoxy)propan-1-ol)di-iso-propylphosphoramidite;
2-cyanoethyl-(3-((1'-chloro)-ferrocenylmethoxy)propan-1-ol)di-iso-propylphosphoramidite;
2-cyanoethyl-(3-((2-tert-butylthio)-ferrocenylmethoxy)propan-1-ol)di-iso-propylphosphoramidite;
2-cyanoethyl-(3-((2-tert-butylsulfinyl)-ferrocenylmethoxy)propan-1-ol)di-iso-propylphosphoramidite;
2-cyanoethyl-(3-((2-tert-butylsulfonyl)-ferrocenylmethoxy)propan-1-ol)di-iso-propylphosphoramidite;
2-cyanoethyl-(3-((2-di-tert-butylphospinyl)-ferrocenylmethoxy)propan-1-ol)di-iso-propylphosphoramidite;
2-cyanoethyl-(3-(2-tributylstannyl-ferrocenylmethoxy)propan-1-ol)di-iso-propylphosphoramidite;
2-cyanoethyl-(3-(2-trimethylsilyl-ferrocenylmethoxy)propan-1-ol)di-iso-propylphosphoramidite;
2-cyanoethyl-(3-(2-tributylsilyl-ferrocenylmethoxy)propan-1-ol)di-iso-propylphosphoramidite;
2-cyanoethyl-(3-(2-trimethylstannyl-ferrocenylmethoxy)propan-1-ol)di-iso-propylphosphoramidite;
2-cyanoethyl-(3-(2-vinyl-ferrocenylmethoxy)propan-1-ol)di-iso-propylphosphoramidite;
2-cyanoethyl-(3-(2-iodo-ferrocenylmethoxy)propan-1-ol)di-iso-propylphosphoramidite;
2-cyanoethyl-(2-(3-ferrocenylpropoxy)ethanol)di-iso-propylphosphoramidite;
2-cyanoethyl-(2-(3-(2-tert-butylthio)-ferrocenylpropoxy)ethanol)di-iso-propylphosphoramidite;
2-cyanoethyl-(2-(3-(2-tert-butylsulfinyl)-ferrocenylpropoxy)ethanol)di-iso-propylphosphoramidite; and
2-cyanoethyl-(2-(3-(2-tert-butylsulfonyl)-ferrocenylpropoxy)ethanol)di-iso-propylphosphoramidite.

3. The compound of claim 1 as an internal control in an electrochemical assay.

4. A method for the manufacture of the compound of claim 1, the method comprising: reacting a compound of formula IA with a functionalising compound to obtain a compound of formula IA' of claim 1, wherein the compound of formula IA is of the following formula:

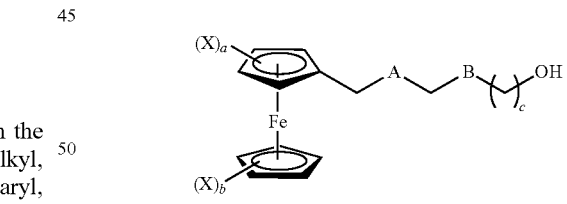

and X, a, b, c, A and B are as defined in claim 1.

5. The compound of claim 1, according to formula IIA:

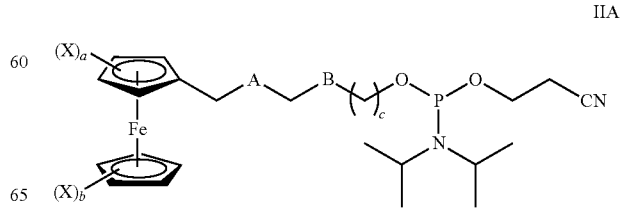

wherein:
each X substituent is independently selected from halo, vinyl, alkyl, cycloalkyl, $SiR_3$, $SnR_3$, $PR_2$, $P(O)R_2$, SR, S(O)R, $SO_2R$, aryl, heteroaryl, CHO, $CO_2R$, CN and $CF_3$;
A is $CH_2$, B is O and c is 2;
a is 0, 1, 2, 3 or 4;
b is 0; and
vinyl, alkyl, cycloalkyl, aryl and heteroaryl may optionally be substituted with 1, 2 or 3 substituents independently selected from unsubstituted OH, CN, fluorine, chlorine, bromine and iodine.

* * * * *